US005770581A

United States Patent [19]
Weichselbaum et al.

[11] Patent Number: 5,770,581
[45] Date of Patent: *Jun. 23, 1998

[54] GENE TRANSCRIPTION AND IONIZING RADIATION: METHODS AND COMPOSITIONS

[75] Inventors: Ralph R. Weichselbaum, Chicago; Dennis E. Hallahan, Park Ridge; Vikas P. Sukhatme, Chicago, all of Ill.; Donald W. Kufe, Wellesley, Mass.

[73] Assignees: Arch Development Corp., Chicago, Ill.; Dana-Farber Cancer Institute, Boston, Mass.

[ * ] Notice: The term of this patent shall not extend beyond the expiration date of Pat. Nos. 5,571,797 and 5,612,318.

[21] Appl. No.: 474,445

[22] Filed: Jun. 7, 1995

Related U.S. Application Data

[60] Division of Ser. No. 943,812, Sep. 11, 1992, which is a continuation-in-part of Ser. No. 633,626, Dec. 20, 1990, abandoned.

[51] Int. Cl.$^6$ ..................................................... A61K 48/00
[52] U.S. Cl. ...................... 514/44; 435/172.3; 536/24.1; 935/36
[58] Field of Search ......................... 514/44; 435/172.3, 435/320.1; 536/24.1; 935/22, 34, 36

[56] References Cited

U.S. PATENT DOCUMENTS

| 4,667,063 | 5/1987 | Mark et al. | 435/68 |
| 5,571,797 | 11/1996 | Ohno et al. | 514/44 |

FOREIGN PATENT DOCUMENTS

WO 94/06916   3/1994   WIPO.

OTHER PUBLICATIONS

Abou–Shoer et al., Flavonoids From *Koelreuteria Henryi* And Other Sources As Protein–Tyrosine Kinase Inhibitors, *J. Nat. Proc.*, 56(6):967–9, 1993.
Alexandropoulos et al., "v–Fps–Responsiveness in the Egr–1 Promoter is Mediated by Serum Response Elements," *Nucleic Acids Research*, 20(9):2355–2359, 1992.
Al–Khodiary and Carr, DNA repair mutants defining $G_2$ checkpoint pathways in *Schizosaccharomyces pombe*, *The EMBO Journal*, 11(4):1343–1350, 1992.
Angel et al., "The jun Proto–Oncogene is Positively Autoregulated by its Product, Jun/AP–1," *Cell*, 55:875–885, 1988.
Atherton–Fessler et al., "Mechanisms of p34$^{cdc2}$ Regulation," *Molecular and Cellular Biology*, 13(3):1675–1685, 1993.
Attar et al., "Expression Cloning of a Novel Zinc Finger Protein that Binds to the c–fos Serum Response Element," *Molecular and Cellular Biology*, 12(5):2432–2443, 1992.
Barbet and Carr, "Fission yeast weel protein kinase is not required for DNA damage–dependent mitotic arrest," *Nature*, 364:824–827, 1993.
Baumann et al., "Response of Xenografts of Human Malignant Gliomas and Squamous Cell Carcinomas to Fractionated Irradiation," *J. Radiation Oncology Biol. Phys.*, 23(4):803–809, 1992.
Beutler and Cerami, "Tumor Necrosis, Cachexia, Shock, and Inflammation: A Common Mediator," *Ann. Rev. Biochem.*, 57:505–518, 1988.
Bhuyan et al., "Lethality, DNA Alkylation, and Cell Cycle Effects of Adozelesin (U–73975) on Rodent and Human Cells," *Cancer Research*, 52:5687–5692, 1992.
Boothman et al., "Identification and Characterization of X–Ray–Induced Proteins in Human Cells," *Cancer Research*, 49:2871–2878, 1989.
Brach et al., "Ionizing Radiation Induces Expression and Binding Activity of the Nuclear Factor *KB*," *J. Clin. Invest.*, 88:691–695, 1991.
Buchdunger et al., "4,5–Dianilinophthalimide: A protein–tyrosine kinase inhibitor with selectivity for the epidermal growth factor receptor signal transduction pathway and potent in vivo antitumor activity," *Proc. natl. Acad. Sci. USA*, 91:2334–2338, 1994.
Budach et al., "The $TCD_{50}$ and Regrowth Delay Assay in Human Tumor Xenografts: Differences and Implications," *Int. J. Radiation Oncology Biol. Phys.*, 25, 259–268, 1993.
Cantley et al., Oncogenes and Signal Transduction, *Cell*, 64:281–302, 1991.
Chan et al., "Selective inhibition of the growth of ras–transformed human bronchial epithelial cells by emodin, a protein–tyrosine kinase inhibitor," *Biochemical and Biophysical Research Communications*, 193(3):1152–1158, 1993.
Chen et al., "Structure of malhamensilipin A, an inhibitor of protein tyrosine kinase, from the cultured chrysophyte *poterioochromonas malhamensis*," *Journal of Natural Products*, 57(4):524–527, 1994.
Datta et al., "Involvement of Reactive Oxygen Intermediates in the Induction of c–jun Gene Transcription by Ionizing Radiation," *Biochemistry*, 31(35):8300–8306, 1992.
Datta et al., "Ionizing Radiation Activates Transcription of the EGR1 Gene Via CarG Elements," *Proc. Natl. Acad. Sci. USA*, 89(21):10149–10153, Nov., 1992.
Datta et al., "Reactive Oxygen Intermediates Target CC(A/T)$_6$GG Sequences to Mediate Activation of the Early Growth Response 1 Transcription Factor Gene by Ionizing Radiation," *Proc. Natl. Acad. Sci. USA*, 90:2419–2422, 1993.

(List continued on next page.)

*Primary Examiner*—Bruce R. Campbell
*Attorney, Agent, or Firm*—Arnold, White & Durkee

[57] ABSTRACT

The present invention provides a DNA molecule comprising a radiation responsive enhancer-promoter operatively linked to an encoding region that encodes at least one polypeptide. An encoding region can comprise a single encoding sequence for a polypeptide or two or more encoding sequences encoding DNA binding, activation or repression domains of a transcription factor. Processes for regulating polypeptide expression and inhibiting tumor growth using such DNA molecules are also provided.

15 Claims, 2 Drawing Sheets

OTHER PUBLICATIONS

Devary et al., "The Mammalian Ultraviolet Response is Triggered by Activation of Src Tyrosine Kinases," *Cell*, 71:1081–1091, 1992.

Enoch and Nurse, "Mutation of Fission Yeast Cell Cycle Control Genes Abolishes Dependence of Mitosis on DNA Replication," *Cell*, 60:665–673, 1990.

Gillespie et al., "Inhibition of pancreatic cancer cell growth in vitro by the tyrphostin group of tyrosine kinase inhibitors," *Br. J. Cancer*, 68:1122–1126, 1993.

Gould et al., "Complementation of the Mitotic Activator, p80$^{cdc25}$, by a Human Protein–Tyrosine Phosphatase," *Science*, 250:1573–1576, 1990.

Gubits et al., "Expression of Immediate Early Genes after Treatment of Human Astrocytoma Cells with Radiation and Taxol," *Int. J. Radiation Oncology Biol. Phys.*, 27(3):637–642, Oct., 1993.

Gustafson et al., "Hydrogen Peroxide Stimulates Phospholipase A$_2$–Mediated Archidonic Acid Release in Cultured Intestinal Epithelial Cells (INT 407)," *Archidonic Acid Release*, 26:237–247, 1991.

Hallahan et al., "Increased tumor necrosis factor α mRNA after cellular exposure to ionizing radiation," *Proc. Natl. Acad. Sci. USA*, 86:10104–10107, 1989.

Hallahan et al., "Inhibition of Protein Kinases Sensitizes Human Tumor Cells to Ionizing Radiation," *Radiation Research*, 129:345–350, 1992.

Hallahan et al., "Ketoconazole Attenuates Radiation–Induction of Tumor Necrosis Factor," *Int. J. Radiation Oncology*, in press, 1994.

Hallahan et al., "Mechanisms of X–Ray Mediated Protooncogene c–jun Expression in Radiation–Induced Human Sarcoma Cell Lines," *Int. J. Radiation Oncology Biol. Phys.*, 21(6):1677–1681, 1991.

Hallahan et al., "Membrane–Derived Second Messenger Regulates X–Ray–Mediated Tumor Necrosis Factor a Gene Induction," *Proc. Natl. Acad. Sci. USA*, 91:4897–4901, May 1994.

Hallahan et al., "Phase I Dose Escalation Study of Tumor Necrosis Factor and Radiation," *International Journal of Radiation Oncology Biology, Physics*, 27(1):184 Abstract 94, 1993.

Hallahan et al., "Protein kinase C mediates x–ray inducibility of nuclear signal transducers EGR1 and JUN," *Proc. Natl. Acad. Sci. USA*, 88:2156–2160, 1991.

Hallahan et al., "Radiation Signaling Mediated by Jun Activation Following Dissociation from a Cell Type–Specific Repressor," *J. Biol. Chem.*, 268(7):4903–4907, Mar. 1993.

Hallahan et al., "The Role of Cytokines in Radiation Oncology," *Important Advances in Oncology*, 1993.

Hallahan et al., "Transcriptional regulation of the TNF gene by x–irradiation," *Proc. Am. Assoc. Cancer Res.*, 31(0):75, 1990.

Hallahan et al., "Tumor Necrosis Factor Gene Expression Is Mediated by Protein Kinase C following Activation by Ionizing Radiation," *Cancer Research*, 51:4565–4569, 1991.

Hartley, et al., "DNA sequence selectivity of guanine–N7 alkylation by nitrogen mustards is preserved in intact cells," *Nucleic Acids Research*, 20(12):3175–3178, 1992.

Hartwell and Weinert, "Checkpoints: Controls that Ensure the Order of Cell Cycle Events," *Science*, 246:629–634, 1989.

Hempel et al., "Tyrosine Phosphorylation of Phospholipase C–1$_2$ upon Cross–linking of Membrane Ig on Murine B Lymphocytes," *The Journal of Immunology*, 148(10):3021–3027, 1992.

Herrlich et al., "DNA Damage–Induced Gene Expression: Signal transduction and Relation to Growth Factor Signaling," *Rev. Physiol. Biochem. Pharmacol.*, 119:187–223, 1992.

Hollander and Fornace, "Induction of fos RNA by DNA–damaging Agents," *Cancer Research*, 49:1687–1692, 1989.

Hsu et al., "Inhibition Kinetics and Selectivity of the Tyrosine Kinase Inhibitor Erbstatin and a Pyridone–Based Analogue," *Biochemical Pharmacology*, 43(11):2471–2477, 1992.

Hwu et al., "Functional and Molecular Characterization of Tumor–Infiltrating Lymphocytes Transduced with Tumor Necrosis Factor–a cDNA for the Gene Therapy of Cancer in Humans," *The Journal of Immunology*, 150(9):4104–4115, May 1993.

Jayasuriya et al., "Emodin, A Protein Tyrosine Kinase Inhibitor From *Polygonum Cuspidatum*," *J. Nat. Proc.*, 55(5):696–8, 1992.

Kastan et al., "Participation of p53 Protein in the Cellular Response to DNA Damage," *Cancer Research*, 51:6304–6311, 1991.

Lambert and Borek, "X–ray–Induced Changes in Gene Expression in Normal and Oncogene–Transformed Rat Cell Lines," *Journal of the National Cancer Institute*, 80(18):1492–1497, 1988.

Luna et al., "Photodynamic Therapy Mediated Induction of Early Response Genes," *Cancer Research*, 54(5):1374–1380, Mar. 1994.

Mustelin and Altman, "Dephosphorylation and Activation of the T Cell Tyrosine Kinase pp56$^{lck}$ by the leukocyte common antigen (CD45)," *Oncogene*, 5:809–813, 1990.

Neta and Oppenheim, "Radioprotection with Cytokines–Learning from Nature to cope with Radiation Damage," *Cancer Cells*, 3(10):391–396, 1991.

Neta et al., "Role of Interleukin 6 (IL–6) in Protection from Lethal Irradiation and in Endocrine Responses to IL–1 and Tumor Necrosis Factor," *The Journal of Experimental Medicine*, 175:689–694, 1992.

Nurse, "Universal Control Mechanism Regulating Onset of M–Phase," *Nature*, 344:503–508, 1990.

Okabe et al., "BE–23372M, A Novel Protein Tyrosine Kinase Inhibitor I. Producing Organism, Fermentation, Isolation and Biological Activities," *The Journal of Antibiotics*, 47(3):289–293, 1994.

Papathanasiou et al., "Identification of an x–ray–inducible human gene and its altered expression in ataxia telangiectasia," *Proceedings of the American Association for Cancer Research*, 31:304, 1990.

Pleiman et al., "Mapping of Sites on the Src Family Protein Tyrosine Kinases p55$^{blk}$, p59$^{fyn}$, and p56$^{lyn}$ Which Interact with the Effector Molecules Phospholipase C–g, Microtubule–Associated Protein Kinase, GTPase–Activating Protein, and Phosphatidylinositol 3–Kinase," *Molecular and Cellular Biology*, 13(9):5877–5887, 1993.

Rewcastle et al., "Tyrosine Kinase Inhibitors. 3. Structure–Activity Relationships for Inhibition of Protein Tyrosine Kinases by Nuclear–Substituted Derivatives of 2,2'–Dithiobis (1–methyl–N–phenyl–1H–indole–3–carboxamide)," *J. Med. Chem.*, 37:2033–2042, 1994.

Sherman et al., "Ionizing Radiation Regulates Expression of the C–Jun Proto–Oncogene," *Proc. Am. Assoc. Cancer Res.*, 31(0):13, Mar. 1990.

Sherman et al., "Regulation of Tumor Necrosis Factor Gene Expression by Ionizing Radiation in Human Myeloid Leukemia Cells and Peripheral Blood Monocytes," *The American Society for Clinical Investigation, Inc.*, 87:1794–1797, 1991.

Sukhatme et al., "A Zinc Finger–Encoding Gene Coregulated with c–fos During Growth and Differentiation, and After Cellular Depolarization," *Cell*, 53:37–43, 1988.

Uckun et al., "Ionizing Radiation Stimulates Unidentified Tyrosine–Specific Protein Kinases in Human B–Lymphocyte Percursors, Triggering Apoptosis and Clonogenic Cell Death," *Proc. Natl. Acad. Sci. USA*, 89:9005–9009, Oct. 1992.

Uckun et al., "Tyrosine phosphorylation is a mandatory proximal step in radiation–induced activation of the protein kinase C signaling pathway in human B–lymphocyte precursors," *Proc. Natl. Acad. Sci. USA*, 90:252–256, 1993.

Ward et al., "The Effect of Steroids on Radiation–Induced Lung Disease in the Rat," *Rad. Res.*, 136:22–28, 1993.

Ward et al., "The Pulmonary Response to Sublethal Thoracic Irradiation in the Rat," *Rad. Res.*, 136:15–21, 1993.

Weichselbaum et al., "Biological Consequences of Gene Regulation After Ionizing Radiation Exposure," *J. of the National Cancer Institute*, 83(7):480–484, 1991.

Weichselbaum et al., "Gene Therapy Targeted by Ionizing Radiation," *Int. J. Radiation Oncology Biol. Phys.*, 24:565–567, 1992.

Weichselbaum et al., "Gene Therapy Targeted by Radiation Preferentially Radiosensitizes Tumor Cells," *Cancer Research*, 54:4266–4269, Aug. 1994.

Weichselbaum et al., "Inherently Radioresistant Cells Exist in Some Human Tumors," *Proc. Natl. Acad. Sci. USA*, 82:4732–4735, 1985.

Weichselbaum et al., "In Vitro Radiobiological Parameters of Human Sarcoma Cell Lines," *Int. J. Radiation Oncology Biol. Phys.*, 15:937–942, 1988.

Weichselbaum, "Possible Applications of Biotechnology to Radiotherapy," *Eur. J. Cancer*, 27(4):405–407, 1991.

Weichselbaum et al., "Radiation induction of immediate early genes: effectors of the radiation–stress response," *Int. J. Rad. Oncol.*, 30:229–234, 1994.

Weichselbaum et al., "Radiation–resistant and repair–proficient human tumor cells may be associated with radiotherapy failure in head–and neck–cancer patients," *Proc. Natl. Acad. Sci. USA*, 83:2684–2688, 1986.

Weichselbaum et al., "X–Ray Sensitivity of Fifty–three Human Diploid Fibroblast Cell Strains from Patients with Characterized Genetic Disorders," *Cancer Research*, 40:920–925, 1980.

Witte et al., Effects of Irradiation on the Release of Growth Factors from Cultured Bovine, Porcine, and Human Endothelial Cells, *Cancer Research*, 49:5066–5072, 1989.

Yamanashi et al., "Activation of Src–like protein–tyrosine kinase Lyn and its association with phosphatidylinositol 3–kinase upon C–cell antigen receptor–mediated signaling," *Proc. Natl. Acad. Sci. USA*, 89:1118–1122, 1992.

Zhou and Elledge, "Isolation of crt Mutants Constitutive for Transcription of the DNA Damage Inducible Gene RNR3 in *Saccharomyces cerevisiae*," *Genetics*, 131:851–866, 1992.

International Search Report dated Dec. 8, 1995 (ARCD:133P—).

Miller et al (1995) FASEB J 9: 190–199.

Culver et al (1994) Trends in Genetics 10: 174–178.

Hodgson (1995) Exp Opin Ther Patents 5: 459–468.

Marshall (1995) Science 269: 1050–1055.

GENE TRANSCRIPTION AND IONIZING RADIATION: METHODS AND COMPOSITIONS

CROSS-REFERENCE TO RELATED APPLICATION

This is a divisional of application Ser. No. 07/943,812, filed Sep. 11, 1992, which is a continuation in part of Ser. No. 07/633,626, filed Dec. 20, 1990, now abandoned.

TECHNICAL FIELD OF THE INVENTION

This invention relates to methods and compositions relating to the regulation of gene transcription and polypeptide expression by ionizing radiation.

BACKGROUND OF THE INVENTION

Certain genes may play a role in the cellular response to stress or DNA-damaging agents. For example, metallothionein I and II, collagenase, and plasminogen activator are induced after UV irradiation (Angel, et al., 1986; 1987; Fornace, et al., 1988a and b; Miskin, et al., 1981). B2 polymerase III transcripts are increased following treatment by heat shock (Fornace, et al., 1986; 1989a). Furthermore, although the level of DNA polymerase β mRNA is increased after treatment with DNA-damaging agents, this transcript is unchanged following irradiation, suggesting that specific DNA-damaging agents differentially regulate gene expression (Fornace, et al., 1989b). Protooncogene c-fos RNA levels are elevated following treatment by UV, heat shock, or chemical carcinogens (Andrews, et al., 1987; Hollander, et al., 1989a). In this regard, the relative rates of fos transcription during heat shock are unchanged, suggesting that this stress increased c-fos RNA through posttranscriptional mechanisms (Hollander, et al., 1989b).

Investigations of the cytotoxic effects of ionizing radiation has focused on the repair of DNA damage or the modification of radiation lethality by hypoxia (Banura, et al., 1976; Moulder, et al., 1984). In prokaryotes and lower eukaryotes, ionizing radiation has been shown to induce expression of several DNA repair genes (Little, et al., 1982); however, induction of gene expression by ionizing radiation has not been described in mammalian cells. DNA-damaging agents other than x-rays induce expression of a variety of genes in higher eukaryotes (Fornace, et al., 1988, 1989; Miskin, et al., 1981).

What is known about the effects of ionizing radiation is that DNA damage and cell killing result. In many examples, the effects are proportional to the dose rate. Ionizing radiation has been postulated to induce multiple biological effects by direct interaction with DNA or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman, et al., 1989). Synthesis of cyclin and coregulated polypeptides is suppressed by ionizing radiation in rat REF52 cells but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

Initiation of mRNA synthesis is a critical control point in the regulation of cellular processes and depends on binding of certain transcriptional regulatory factors to specific DNA sequences. However, little is known about the regulation of transcriptional control by ionizing radiation exposure in eukaryotic cells. The effects of ionizing radiation on post-transcriptional regulation of mammalian gene expression are also unknown.

Many diseases, conditions, and metabolic deficiencies would benefit from destruction, alteration, or inactivation of affected cells, or by replacement of a missing or abnormal gene product. In certain situations, the affected cells are focused in a recognizable tissue. Current methods of therapy which attempt to seek and destroy those tissues, or to deliver necessary gene products to them, have serious limitations. For some diseases, e.g., cancer, ionizing radiation is useful as a therapy. Methods to enhance the effects of radiation, thereby reducing the necessary dose, would greatly benefit cancer patients. Therefore, methods and compositions were sought to enhance radiation effects by investigating effects of radiation on gene expression. A goal was to provide new types of therapy using radiation, and to explore other uses of radiation.

BRIEF SUMMARY OF THE INVENTION

In one aspect, the present invention relates to a synthetic DNA molecule comprising a radiation responsive enhancer-promoter operatively linked to an encoding region that encodes at least one polypeptide, which encoding region is operatively linked to a transcription-terminating region.

Preferably, a radiation responsive enhancer-promoter comprises a CArG domain of an Egr-1 promoter, a TNF-α promoter or a c-Jun promoter. In one preferred embodiment, an encoding region encodes a single polypeptide. A preferred polypeptide encoded by such an encoding region has the ability to inhibit the growth of a cell and, particularly a tumor cell.

An exemplary and preferred polypeptide is a cytokine, a dominant negative, a tumor suppressing factor, an angiogenesis inhibitor or a monocyte chemoattractant. More particularly, such a preferred polypeptide is TNF-α, interleukin-4, JE, ricin, PF4 Pseudomonas toxin, p53, the retinoblastoma gene product or the Wilms' tumor gene product.

Another preferred polypeptide encoded by such an encoding region has radioprotective activity toward normal tissue. An exemplary and preferred such polypeptide having radioprotective activity is interleukin-1; TNF; a tissue growth factor such as a hematopoietic growth factor, a hepatocyte growth factor, a kidney growth factor, an endothelial growth factor or a vascular smooth muscle growth factor; interleukin-6; a free radical scavenger or a tissue growth factor receptor.

Preferably, 1) a hematopoietic growth factor is interleukin-3 or a colony stimulating factor (CSF) such as GM-CSF, G-CSF and M-CSF; 2) an endothelial growth factor is basic fibroblast growth factor (bFGF); 3) a vascular smooth muscle growth factor is platelet derived growth factor (PDGF); and 4) a free radical scavenger is manganese superoxide dismutase (MnSOD).

Yet another preferred polypeptide encoded by such an encoding region has anticoagulant, thrombolytic or thrombotic activity as exemplified by plasminogen activator, a streptokinase or a plasminogen activator inhibitor.

A further preferred polypeptide encoded by such an encoding region has the ability to catalyze the conversion of a pro-drug to a drug. Exemplary and preferred such polypeptides are herpes simplex virus thymidine kinase and a cytosine deaminase.

A further preferred polypeptide encoded by such an encoding region is a surface antigen that is a gene product of a major histocompatibility complex. Exemplary and preferred such polypeptides are H2 proteins and HLA protein.

In another aspect, an encoding region of a DNA molecule of the present invention encodes the whole or a portion of more than one polypeptide. Preferably, those polypeptides are transcription factors. In accordance with such an embodiment, an encoding region comprises:

(a) a first encoding sequence that encodes a DNA binding domain of a first transcription factor;

(b) a second encoding sequence that encodes an activation or repression domain of a second transcription factor;

(c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (d) a transcription-terminating region that is operatively linked to any of the first, second or third encoding sequences such that the transcription-terminating region is located 3' to all of the first, second and third encoding sequences.

In a preferred embodiment, a first encoding sequence encodes a DNA binding domain of transcription factor GAL4, a second encoding sequence encodes the VP-16 activation domain, the NF-κB activation domain, the repression domain of the Wilms' tumor suppressor gene WT1 or the repression domain of Egr-1.

In yet another aspect, a DNA molecule of the present invention comprises a binding region that is capable of binding a DNA binding domain of a transcription factor, which binding region is operatively linked to a minimal promoter that is operatively linked to an encoding region that encodes a polypeptide, which encoding region is operatively linked to a transcription-terminating region.

Preferably, the transcription factor is GAL4 and the polypeptide is the same as set forth above.

The present invention also contemplates a pharmaceutical composition comprising a DNA molecule of the present invention and a physiologically acceptable carrier.

In another aspect, the present invention contemplates a cell transformed or transfected with a DNA molecule of this invention or a transgenic cell derived from such a transformed or transfected cell. Preferably, a transformed or transgenic cell of the present invention is a leukocyte such as a tumor infiltrating lymphocyte or a T cell or a tumor cell.

In another aspect, the present invention contemplates a process of regulating the expression of a polypeptide comprising the steps of:

(a) operatively linking a radiation responsive enhancer-promoter to an encoding region that encodes the polypeptide, which encoding region is operatively linked to a transcription-terminating region to form a DNA molecule; and (b) exposing the DNA molecule to an effective expression-inducing dose of ionizing radiation.

In an alternate embodiment, more than one DNA molecule is prepared. Preferably, those DNA molecules comprise:

(1) a first DNA molecule comprising a radiation responsive enhancer-promoter operatively linked to an encoding region that comprises:
   (a) a first encoding sequence that encodes a DNA binding domain of a first transcription factor;
   (b) a second encoding sequence that encodes an activation or repression domain of a second transcription factor;
   (c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and
   (d) a transcription-terminating region that is operatively linked to any of the first, second or third encoding sequences such that the transcription-terminating region is located 3' to all of the first, second and third encoding sequences; and (2) a second DNA molecule comprising a binding region that is capable of binding the DNA binding domain of the first transcription factor, which binding region is operatively linked to a minimal promoter that is operatively linked to an encoding region that encodes a polypeptide, which encoding region is operatively linked to a transcription-terminating region.

A radiation responsive enhancer-promoter, a transcription factor, a binding domain of a transcription factor and an activation or repression domain of a transcription factor are preferably those set forth above. A polypeptide encoded by an encoding region is also preferably the same as set forth above.

Where regulating is inhibiting, an encoding region preferably comprises:

(a) a first encoding sequence that encodes a DNA binding domain of positively acting transcription factor for a gene encoding the polypeptide;

(b) a second encoding sequence that encodes a repression domain of a transcription factor;

(c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (d) a transcription-terminating region that is operatively linked to any of the first, second or third encoding sequences such that the transcription-terminating region is located 3' to all of the first, second and third encoding sequences.

Preferably the second encoding sequence encodes the repression domain of the Wilms' tumor suppressor gene WT1 or the repression domain of Egr-1.

In yet another aspect the present invention contemplates a process of inhibiting growth of a tumor comprising the steps of:

(a) delivering to the tumor a therapeutically effective amount of a DNA molecule comprising a radiation responsive enhancer-promoter operatively linked to an encoding region that encodes a polypeptide having the ability to inhibit the growth of a tumor cell, which encoding region is operatively linked to a transcription-terminating region; and (b) exposing the tumor to an effective expression-inducing dose of ionizing radiation.

Preferably, a radiation responsive enhancer-promoter comprises a CArG domain of an Egr-1 promoter, a TNF-α promoter or a c-Jun promoter and a polypeptide is a cytokine, a dominant negative, a tumor suppressing factor or an angiogenesis inhibitor.

Delivering is preferably introducing the DNA molecule into the tumor. Where the tumor is in a subject, delivering is administering the DNA molecule into the circulatory system of the subject. In a preferred embodiment, administering comprises the steps of:

(a) providing a vehicle that contains the DNA molecule; and (b) administering the vehicle to the subject.

A vehicle is preferably a cell transformed or transfected with the DNA molecule. An exemplary and preferred transformed or transfected cell is a leukocyte such as a tumor infiltrating lymphocyte or a T cell or a tumor cell from the tumor being treated. Alternatively, the vehicle is a virus or an antibody that immunoreacts with an antigen of the tumor.

In a preferred embodiment, exposing comprises the steps of:

a) providing a radiolabelled antibody that immunoreacts with an antigen of the tumor; and b) delivering an effective expression inducing amount of the radiolabelled antibody to the tumor.

Alternatively, a process of inhibiting growth of a tumor comprises the steps of:

(a) delivering to the tumor a therapeutically effective amount of (1) a first DNA molecule comprising a radiation responsive enhancer-promoter operatively linked to an encoding region that comprises:

(i) a first encoding sequence that encodes a DNA binding domain of a first transcription factor;

(ii) a second encoding sequence that encodes an activation or repression domain of a second transcription factor;

(iii) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (iv) a transcription-terminating region that is operatively linked to any of the first, second or third encoding sequences such that the transcription-terminating region is located 3' to all of the first, second and third encoding sequences; and (2) a second DNA molecule comprising a binding region that is capable of binding the DNA binding domain of the first transcription factor, which binding region is operatively linked to a minimal promoter that is operatively linked to an encoding region that encodes a polypeptide that has the ability to inhibit the growth of a tumor cell, which encoding region is operatively linked to a transcription-terminating region; and (b) exposing the cell to an effective expression-inducing dose of ionizing radiation.

Preferably, a radiation responsive enhancer-promoter and a polypeptide are the same as set forth above. Delivering is preferably the same as set forth above.

BRIEF DESCRIPTION OF THE DRAWINGS

In the drawings, which form a portion of the specification.

DETAILED DESCRIPTION OF THE INVENTION

I. The Invention

Figure 1A:
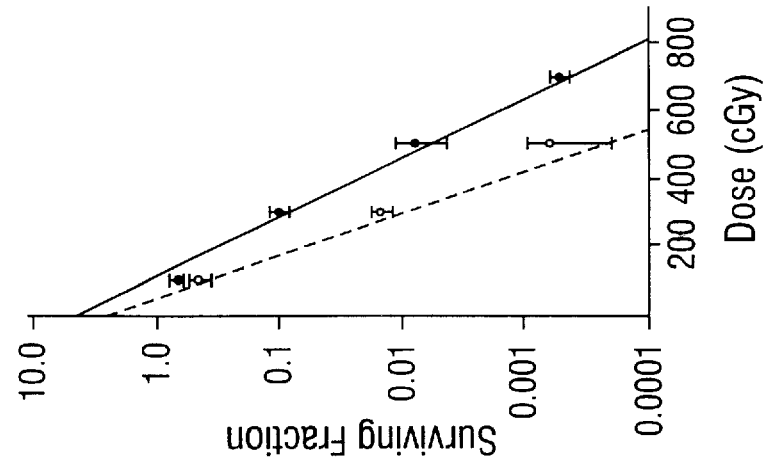
FIG. 1 depicts the influence of TNF-α on radiation lethality of TNF-α-producing human sarcomas and TNF-α-nonproducing human tumor cells.

The present invention relates to compositions and methods for regulating transcription of an encoding DNA sequence and expression of a polypeptide encoded by that sequence. A composition of the present invention comprises one or more synthetic DNA molecules comprising an enhancer-promoter region that is responsive to ionizing radiation and an encoding region that encodes at least one polypeptide. In this invention, control is exerted over transcription of an encoding DNA sequence by an enhancer-promoter region responsive to ionizing radiation. The enhancer-promoter region is used as a switch to selectively affect expression of a polypeptide encoded by that sequence. The regulation of specific polypeptide expression in a distinct target cell or tissue provides opportunities for therapeutic destruction, alteration, or inactivation of that cell or tissue.

A. DNA Molecules

In one aspect, the present invention contemplates a synthetic DNA molecule comprising a radiation responsive enhancer-promoter operatively linked to an encoding region that encodes at least one polypeptide, which encoding region is operatively linked to a transcription terminating region. As used herein, the term "synthetic" indicates that a DNA molecule of the present invention is man-made (not naturally occuring) by any means including but not limited to de novo synthesis. Preferably, that synthetic DNA molecule is isolated and purified and exists substantially free of other nucleic acids, proteins and the like.

1. Radiation responsive enhancer-promoter

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit. Exemplary and preferred promoters are the TATA box, the CAAT box and GC-rich sequence elements.

Another type of discrete transcription regulatory sequence element is an enhancer. An enhancer provides specificity of time, location and expression level for a particular encoding region (e.g., gene). A major function of an enhancer is to increase the level of transcription of an encoding region in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. As used herein, a "radiation responsive enhancer-promoter" indicates an enhancer-promoter whose transcription controlling function is affected by ionizing radiation. Typically, upon exposure to an effective dose of ionizing radiation, a radiation responsive enhancer-promoter of the present invention stimulates or increases the rate of transcription of an encoding region controlled by that enhancer-promoter. An exemplary and preferred enhancer-promoter for use in a DNA molecule of the present invention is a CArG domain of an Egr-1 promoter, a promoter for tumor necrosis factor-alpha (TNF-α) gene or a c-Jun promoter.

a. CArG Domain of Egr-1 Promoter

Exposure of mammalian cells to ionizing radiation is associated with induction of Egr-1 gene expression. The Egr-1 gene (also known as zif/268, TIS-8, NFGI-A and Krox-24; Sukhatme, et al. 1988; Christy, et al., 1988; Milbrandt, 1987; Lemaire, et al., 1988; Lim, et al., 1987; Gessler, 1990) encodes a 533-amino acid residue nuclear phosphoprotein with a $Cys_2$-$His_2$ zinc finger domain that is partially homologous to the corresponding domain in the Wilms' tumor-susceptibility gene (Gessler, 1990). The Egr-1 protein binds to the DNA sequence CGCCCCCGC in a zinc-dependent manner and functions as a regulator of gene transcription (Christy, et al., 1989; Cao, et al., 1990; Lau, et al., 1987). Both mitogenic and differentiation signals have been shown to induce the rapid and transient expression of Egr-1 in a variety of cell types. Exposure of human HL-525 cells to x-rays was associated with increases in Egr-1 mRNA levels. Those increases were maximal at 3 hours and transient. Nuclear run-on assays demonstrated that this effect was related at least in part to activation of Egr-1 gene transcription.

Sequences responsive to ionizing radiation-induced signals were determined by deletion analysis of the Egr-1 promoter. X-ray inducibility of the Egr-1 gene was conferred by a region containing six serum response or $CC(A/T)_6GG$ (CArG) domains or domains.

A region encompassing the three distal or upstream CArG elements was functional in the x-ray response as sequential deletion of those three CArG domains progressively decreased the response. A single CArG domain, however, was found to be sufficient to confer X-ray inducibility. Those results indicate that ionizing radiation induces Egr-1 transcription through one or more CArG domains.

In order to identify cis elements responsible for x-ray-induced Egr-1 transcription, the Egr-1 promoter region extending from position −957 upstream to the transcription start site to position +248 was ligated to a chloramphenicol acetyl transferase (CAT) reporter gene to form plasmid pEgr1 P1.2. The Egr-1 promoter region contains several putative cis elements including six CArG domains (Christy, et al., 1989; Qureshi, et al., 1991). Treatment of pEgr-1 P1.2 transfected cells with ionizing radiation was associated with a 4.1-fold increase in CAT activity as compared to transfected but unirradiated cells. In contrast, similar studies performed with plasmid pΔEgr-1 P1.2 (similar to pEgr-1 P1.2 except that nucleotides from position −550 to −50 are deleted) demonstrated little if any inducibility by x-rays. Thus, x-ray inducibility of Egr-1 is likely mediated by sequences present between −550 and −50 of the Egr-1 promoter.

Irradiation of cells transfected with plasmid pE425, which plasmid contains an about 491 base pair region of the Egr-1 promoter with six CArG domains operatively linked to a CAT gene, was associated with a 3.6-fold induction of CAT activity compared to that in non-irradiated cells transfected with this construct.

Figure 2:
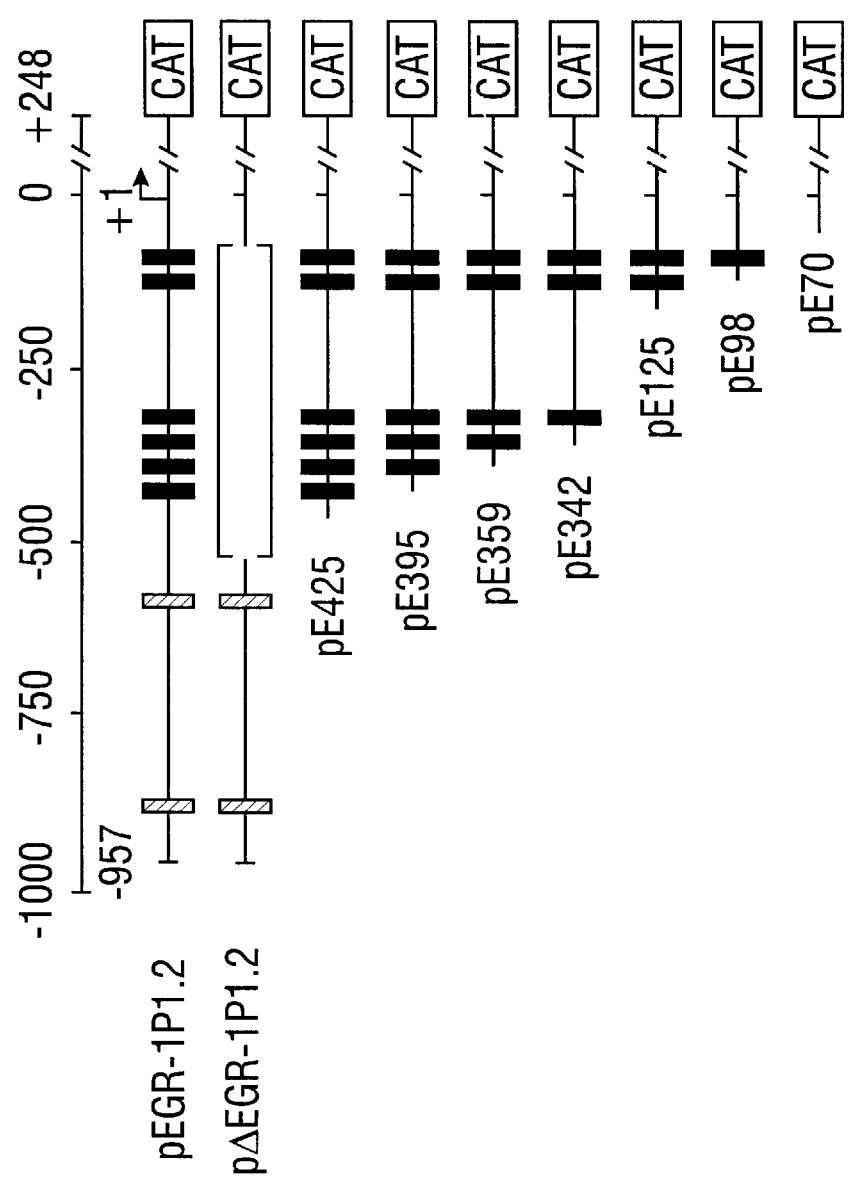
FIG. 2 depicts Scheme I which shows a series of deleted Egr-1 promoter constructs.

A series of deleted Egr-1 promoter constructs was next used to further define the x-ray responsive elements in pE425. Those constructs are shown schematically in Scheme 1, depicted in FIG. 2.

In Scheme 1 (FIG. 2), vertical black rectangles indicate CArG domains of the indicated plasmids. An encoding region for CAT is shown at the 3' and of each molecule. Brackets indicate deletions relative to the promoter region of Egr-1 shown schematically at the top of the scheme. Numbers indicate nucleotide positions relative to the transcription start site (indicated by the number 0).

Where cells were transfected with constructs having sequential deletion of the three distal CArG domains, X-ray inducibility of CAT activity progressively decreased. Transfection with plasmid pE395 (first CArG deleted) conferred x-ray inducibility to a lesser extent than transfection with pE425. Transfection with plasmid pE359 (deletion of the first and second CArG domains) resulted in further decreases in induced CAT activity. Transfection with plasmid pE342 (deletion of the first three CArG domains) was associated with minimal induction of CAT activity.

Other studies were performed with fragments of the Egr-1 promoter linked to elements of a herpes simplex virus-thymidine kinase (HSV-TK) gene and the CAT gene. There was no detectable x-ray inducibility of CAT activity in cells transfected with plasmid pTK35CAT (containing a thymidine kinase promoter but no Egr-1 promoter regions). In contrast, cells transfected with plasmid pE425/250TK (containing the four distal CArG domains and using HSV-TK promoter), CAT activity was inducible by x-rays. The region of the Egr-1 promoter extending from −395 to −250, which region excludes the first CArG element, was also functional in conferring x-ray inducibility to the heterologous promoter.

Although those findings provided further support for the involvement of CArG domains in x-ray induced Egr-1 transcription, other sequences between these domains could also serve as functional cis elements. Transfection of cells with plasmid pSRE1TK (containing the first CArG domain having seven base pairs of the 5' and 3' flanking sequences) induced transcription of pTK35CAT.

Thus, x-ray inducibility of the Egr-1 gene is conferred by a region of the Egr-1 promoter that contains CArG domains. The six CArG domains of the Egr-1 promoter are located within a region of the Egr-1 promoter located about 960 nucleotide bases upstream from the transcription initiation site of the Egr-1 gene. A single CArG domain is sufficient to confer radiation inducibility. Preferably, a radiation responsive enhancer-promoter comprises at least one of the three most distal (i.e. upstream) CArG domains. A detailed description of the radiation inducibility of the Egr-1 gene by CArG domains upstream to the transcription initiation site can be found in Example 4 hereinafter.

Studies with the c-fos promoter have demonstrated that the CArG domain or serum response element is functional in inducing transcription of this gene in response to serum and other signals (Triesman, 1990). The CArG element is required for c-fos induction by both PKC-mediated signaling pathways and by growth factor-induced signals independent of PKC (Fisch, et al., 1987; Gilman, 1988; Buscher, et al., 1988; Sheng, et al., 1988; Stumpo, et al., 1988; Graham, et al., 1991). The kinetics of induction, as well as repression, of c-fos expression are similar to those of Egr-1 in other models (Sukhatme, et al., 1988; Guis, et al., 1990). Indeed, x-ray-induced changes in c-fos transcripts are similar to those obtained for Egr-1 in HL-525 cells and TPA-induced c-fos expression, like that for Egr-1, is attenuated in these cells. Studies with the c-fos promoter have demonstrated that the CArG domain functions as a binding site for the serum response factor (SRF) (Treisman, 1986; Prywes, et al., 1988). SRF binds, but with varying affinity, to the different CArG elements in the Egr-1 promoter (Christy, et al., 1989).

Previous studies have demonstrated that binding of SRF to CArG in the c-fos promoter is not detectably altered by serum and other conditions (Treisman, 1986; Prywes, et al., 1986; Sheng, et al., 1988). Nuclear proteins from quiescent and serum-stimulated 3T3 cells have also shown little if any difference in binding to the first CArG element of the Egr-1 promoter (Gius, et al., 1990). These findings suggest that ionizing radiation, like serum, induces a posttranscriptional modification of SRF. Other studies have demonstrated that phosphorylation of SRF is required for activation or transcription (Prywes, et al., 1988). The kinases responsible for this effect, however, remain unclear.

Alternatively, ionizing radiation may result in the modification of other proteins that interact with the SRF or CArG domain. Both SAP-1 and $p62^{TCF}$ (ternary complex factor) recognize SRF-DNA complexes (Dalton, et al., 1992; Shaw, et al., 1989), while $p62^{DBF}$ (direct binding factor) binds directly to the SRE (Ryan, et al., 1989; Walsh, 1989). Other studies have demonstrated that SRE-ZBP undergoes post-translational modification and binds to this element (Attar, et al., 1992). One or more of these proteins may therefore be involved in x-ray-induced Egr-1 transcription.

b. c-Jun promoter

Exposure of cells to x-rays is associated with activation of the c-Jun/c-fos gene families, which encode transcription factors (Hallahan, et al., 1991; Sherman, et al., 1990).

The c-Jun gene encodes the major form of the 40–44 kD AP-1 transcription factor (Mitchell, et al., 1989). The Jun/AP-1 complex binds to the heptomeric DNA consensus sequence $TGA^G/_CTCA$ (Mitchell, et al., 1989). The DNA binding domain of c-Jun is shared by a family of transcription factors, including Jun-B, Jun-D and c-fos. Moreover, the affinity of c-Jun binding to DNA is related to the formation of homodimers or heterodimers with products of the fos gene family (Zorial, et al., 1989; Nakabeppa, et al., 1988; Halazonetis, et al., 1988).

Phorbol ester activation of c-Jun transcription in diverse cell types has implicated the involvement of a protein kinase C (PKC)-dependent mechanism (Brenner, et al., 1989; Angel, et al., 1988b; Hallahan, et al., 1991a). A similar pathway likely plays a role, at least in part, in the induction of c-Jun expression by ionizing radiation. Prolonged treatment with phorbol esters to down-regulate PKC is associated with decreases in the effects of x-rays on c-Jun transcription (Hallahan, et al., 1991a). Furthermore, non-specific inhibitors of PKC, such as the isoquinolinesulfonamide derivative, H7, block x-ray-induced c-Jun gene product expression (Hallahan, et al., 1991a).

The effects of ionizing radiation on c-Jun gene product expression were studied in an HL-60 cell variant, designated HL-525, which variant is deficient in PKC-mediated signal transduction (Homma, et al., 1986). That variant is resistant to both phorbol ester-induced differentiation and x-ray-induced TNF gene product expression (Hallahan, et al., 1991b; Homma, et al., 1986) and resistant to the induction of c-Jun gene product expression by phorbol esters.

Treatment of those cells with ionizing radiation was associated with a superinduction of c-Jun mRNA levels compared to phorbol ester-responsive HL-60 cells. Transcription of c-Jun was low in untreated HL-525 cells. However, exposure of those cells to ionizing radiation resulted in c-Jun mRNA levels which were substantially higher at 3, 6 and 8 hours after x-ray exposure than in non-irradiated cells. Expression of the Jun-B and Jun-D gene products was also transiently increased following x-irradiation of the HL-525 cells. The kinetics of those increases in fos gene product expression were similar to that obtained for members of the Jun gene family.

The activation of Jun likely results in increased transcription of the AP-1 binding site following ionizing radiation exposure. The plasmid p3xTRE-CAT (containing three AP-1 sites upstream of the minimal tk promoter from plasmid pBLCAT2) was transfected into RIT-3 cells. Irradiation of p3xTRE-CAT transfectants resulted in a 3-fold increase in CAT expression.

Where RIT-3 cells transfected with a DNA molecule (c-Jun-CAT) comprising a 1840-base pair (−1.1 kb to +740 bp) segment of the c-Jun promoter placed upstream of the CAT gene were exposed to ionizing radiation, CAT expression increased about 3-fold relative to transfected, non-irradiated cells. Transfection of those cells with a plasmid having a deletion of the AP-1 site located at +150-bp (−132/+170ΔAP-1CAT) resulted in a loss of x-ray-mediated induction of CAT expression. Thus, activated AP-1 likely participates in the transcription of c-Jun and the AP-1 DNA sequence is likely sufficient and necessary to confer x-ray-mediated c-Jun gene induction. A detailed description of x-ray induced transcription of DNA molecules containing a c-Jun promoter can be found hereinafter in Examples 2, 3, 5 and 6.

c. TNF-α promoter

Tumor necrosis factor a (TNF-α) is a polypeptide mediator of the cellular immune response with pleiotropic activity. TNF-α acts directly on vascular endothelium to increase the adhesion of leukocytes during the inflammatory process (Bevelacqua, et al., 1989). This in vivo response to TNF-α was suggested to be responsible for hemorrhagic necrosis and regression of transplantable mouse and human tumors (Carswell, 1975). TNF-α also has a direct effect on human cancer cell lines in vitro, resulting in cell death and growth inhibition (Sugarman, et al., 1985; Old, 1985). The cytotoxic effect of TNF-α correlates with free-radical formation, DNA fragmentation, and microtubule destruction (Matthews, et al., 1988; Rubin, et al., 1988; Scanlon, et al., 1989; Yamauchi, et al., 1989; Matthews, et al., 1987; Neale, et al., 1988). Cell lines that are resistant to oxidative damage by TNF-α also have elevated free-radical buffering capacity (Zimmerman, et al., 1989; Wong, et al., 1988).

In addition, TNF-α causes hydroxyl radical production in cells sensitive to killing by TNF-α (Matthews, et al., 1987). Cell lines sensitive to the oxidative damage produced by TNF-α have diminished radical-buffering capacity after TNF-α is added (Yamauchi, et al., 1989). Lower levels of hydroxyl radicals have been measured in cells resistant to TNF-α cytotoxicity when compared with cells sensitive to TNF-α killing (Matthews, et al., 1987).

TNF-α is increased after treatment with x-rays in certain human sarcoma cells (e.g., STSAR-13 and STSAR-48). TNF-α mRNA levels were substantially elevated 3 and 6 hours after irradiation of STSAR-13 and STSAR-48 cells. TNF-α mRNA levels in cell line STSAR-13 increased by >2.5-fold as measured by densitometry 3 hours after exposure to 500 cGy and then declined to baseline levels by 6 hours. TNF-α transcripts increased at 6 hours after irradiation in cell line STSAR-48, thus indicating some heterogeneity between cell lines in terms of the kinetics of TNF-α gene expression. In contrast, irradiation had no detectable effect on 7S RNA levels or expression of the polymerase β gene.

The increase in TNF-α mRNA was accompanied by an increased expression of TNF-α protein, which increase was accompanied by secretion of TNF-α protein into the medium in which those cells were grown. Levels of TNF-α in the medium of human tumor cell lines and fibroblasts were quantified before and after exposure to ionizing radiation. Five of 13 human bone and soft tissue sarcoma cell lines (STSAR-5, -13, -33, -43, and -48) released TNF-α into the medium after irradiation, whereas TNF-α levels were not elevated in supernatant from normal human fibroblast cell lines (GM-1522 and NHF-235) and four human epithelial tumor cell lines (HN-SCC-68, SCC-61, SCC-25, and SQ-20B) after exposure to radiation. Tumor cell line STSAR-13 produced undetectable amounts of TNF-α before x-irradiation and 0.35 units/ml after x-ray exposure. Cell lines STSAR-5 and -33 responded to x-irradiation with increases in TNF-α concentrations of >5- to 10-fold. Cell lines STSAR-43 and -48 demonstrated increases in TNF-α of 1.5- to 3-fold. TNF-α protein in the medium was first elevated at 20 hr after x-ray treatment, reached maximal levels at 3 days, and remained elevated beyond 5 days. Furthermore, supernatant from irradiated, but not control STSAR-33 cells, was cytotoxic to TNF-α-sensitive cell line SQ-20B. A detailed description of x-ray induced transcription of DNA molecules containing the TNF-α promoter can be found hereinafter in Example 1.

2. Encoding Region

A radiation responsive enhancer-promoter is operatively linked to an encoding region that encodes at least one polypeptide. As used herein, the phrase "operatively linked" means that an enhancer-promoter is connected to an encoding region in such a way that the transcription of that encoding region is controlled and regulated by that enhancer-promoter. Means for operatively linking an enhancer-promoter to an encoding region are well known in the art. As is also well known in the art, the precise orientation and location relative to an encoding region whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

a. Single polypeptide

In one embodiment, an encoding region of a DNA molecule of the present invention encodes a single polypeptide. As used herein, the term "polypeptide" means a polymer of amino acids connected by amide linkages, wherein the number of amino acid residues can range from about 5 to about one million. Preferably, a polypeptide has from about 10 to about 1000 amino acid residues and, even more preferably from about 20 to about 500 amino residues. Thus, as used herein, a polypeptide includes what is often referred to in the art as an oligopeptide (5–10 amino acid residues), a polypeptide (11–100 amino acid residues) and a protein (>100 amino acid residues). A polypeptide encoded by an encoding region can undergo post-translational modification to form conjugates with carbohydrates, lipids, nucleic acids and the like to form glycopolypeptides (e.g., glycoproteins), lipopolypeptides (e.g. lipoproteins) and other like conjugates.

Any polypeptide can be encoded by an encoding region of a DNA molecule of the present invention. An encoding region can comprise introns and exons so long as the encoding region comprises at least one open reading frame for transcription, translation and expression of that polypeptide. Thus, an encoding region can comprise a gene, a split gene or a cDNA molecule. In the event that the encoding region comprises a split gene (contains one or more introns), a cell transformed or transfected with a DNA molecule containing that split gene must have means for removing those introns and splicing together the exons in the RNA transcript from that DNA molecule if expression of that gene product is desired.

In a preferred embodiment, a polypeptide encoded by an encoding region of a DNA molecule of the present invention interferes with the structural or functional integrity of a cell exposed to that polypeptide. Such a polypeptide has the ability to inhibit the growth of a cell and, particularly a tumor cell. A polypeptide is preferably a cytokine, a dominant negative, a tumor suppressing factor, an angiogenesis inhibitor, or a monocyte chemoattractant.

Dominant negatives to cellular enzymes such as Raf-1 kinase are cytotoxic to human tumor cells (Qureshi, et al., 1991). Dominant negatives to oncogenes such as N-myc may also be effective in the treatment of cancer.

Expression of tumor suppressor genes such as p53, the retinoblastoma (Rb) susceptibility gene, Wilms' tumor gene can be controlled by radiation. Transfection of p53 deficient tumor cells with a p53 expression vector abrogates cell growth (Johnson, et al., 1991).

Tumor growth is angiogenesis-dependent and angiogenesis is directly or indirectly induced by the tumor. Induction of angiogenesis is an important step in carcinogenesis and in metastatic development. Angiogenesis is induced during the transition from hyperplasia to neoplasia. Since angiogenesis is necessary for tumor growth, any natural or synthetic antiangiogenic compound may have an antineoplastic potential. Inhibition of tumor angiogenesis through controlled expression of an anti-angiogenesis gene could play an important role in cancer treatment. Inhibitors of capillary endothelial cell proliferation and/or angiogenesis are a cartilage-derived inhibitor and platelet factor 4 (PF4) (reviewed in Neta, et al., 1991; Zucker, et al., 1991).

The mouse fibroblast gene is induced by PDGF. The fibroblast gene product, JE or monocyte chemoattractant protein-1 (MCP-1) is a member of a family of cytokine-like glycoproteins whose expression is induced by a mitogenic signal in monocytes, macrophages and T cells. JE has been identified, characterized and recombinantly produced from both mouse and human fibroblasts (Rollins et al., 1989). The mouse and human fibroblast gene products are designated mJE and hJE, respectively.

MCP-1 or JE is a monocyte-specific chemoattractant in vitro that is structurally related to a family of proinflammatory cytokines such as macrophage inflammatory proteins.

Exemplary and preferred polypeptides are tumor necrosis factor (TNF), interleukin-4, JE, PF4 ricin, a bacterial toxin such as Pseudomonas toxin; p53, the retinoblastoma gene product or the Wilms' tumor gene product.

In another preferred embodiment a polypeptide encoded by an encoding region has radioprotective activity toward normal cells (i.e., the polypeptide protects a normal cell or tissue from a deleterious effect of radiation). Exemplary and preferred polypeptides having radioprotective activity are interleukin-1; tumor necrosis factor; a tissue growth factor such as a hematopoietic growth factor, a hepatocyte growth factor, a kidney growth factor, an endothelial growth factor or a vascular smooth muscle growth factor; interleukin-6, a free radical scavenger or a tissue growth factor receptor.

Preferably, 1) a hematopoietic growth factor is a colony stimulating factor such as GM-CSF, G-CSF, M-CSF or interleukin-3; 2) an endothelial growth factor is basic fibroblast growth factor; 3) a vascular smooth muscle growth factor is platelet derived growth factor (PDGF); and 4) a free radical scavenger is manganese superoxide dismutase (MnSOD).

The radioprotective effect of administered IL-1 and IL-6 have been demonstrated (Neta, et al., 1991; Neta, et al., 1992). The added benefit of radioprotection of hematopoietic cells was demonstrated by exogenous TNF added prior to irradiation which has been demonstrated to protect the hematopoietic system in animals (Neta, et al., 1991).

Studies by Neta et al have demonstrated that IL-1 induces several hematopoietic growth factors (GM-CSF, G-CSF, M-CSF, IL 3, and IL 6) which clearly contribute to the accelerated growth and differentiation of hematopoietic progenitor cells (Neta, et al, 1991). Uckun et al have examined the radioprotective effects of pre-total body irradiation (TBI) conditioning with recombinant granulocyte colony-stimulating factor (rG-CSF) and recombinant granulocyte-macrophage CSF (rGM-CSF) in a large series of lethally irradiated mice (Uckun, et al, 1989). Administration of rG-CSF or rGM-CSF before TBI protects a significant fraction of mice from the lethal effects of LD 100/30 TBI (Waddick, et al., 1991). At equivalent doses, rG-CSF displayed a more potent radioprotective activity than rGM-CSF. The survival rate after lethal TBI was also significantly higher in mice receiving optimally radioprotective doses of rG-CSF as compared with mice receiving optimally radioprotective doses of rGM-CSF. Pretreatment with rG-CSF followed by rGM-CSF was slightly more effective than rG-CSF alone in supralethally irradiated mice but not in lethally irradiated mice. Neta et al. have also shown that administration of suboptimal, nonradioprotective doses of IL-1 alpha also synergize with GM-CSF or G-CSF to confer optimal radioprotection (Neta, et al., 1988), suggesting that such an interaction may be necessary for radioprotection of hemopoietic progenitor cells.

TNF may induce radioprotection through the production of manganese superoxide dismutase (MnSOD), which has been shown to be associated with radiation resistance in the T-cell line HUT-78 (Wong, et al., 1991). C-met is the receptor for hepatocyte growth factor and is activated during kidney and liver regeneration. These genes can be used to prevent radiation injury to these organs.

Arteriovenous malformations (AVMs) in the cerebrum have been treated with radiosurgery. This technology involves the direction of high dose irradiation to the AVM. The intima of AVMs thickens through endothelial proliferation and the microvasculature is obliterated (Steiner, 1984). Endothelial and smooth muscle proliferation have been shown to be associated with the production of bFGF and PDGF. Clinical results may be improved by the addition of bFGF and PDGF.

In yet another preferred embodiment, the polypeptide encoded by the encoding region has anticoagulant, thrombolytic or thrombotic activity as exemplified by plasminogen activator, a streptokinase or a plasminogen activator inhibitor.

The value of coronary artery reperfusion resulting from pharmacologically induced fibrinolysis in patients with evolving myocardial infarction has been rigorously evaluated (reviewed in Tiefenbrunn, 1992; Becker, et al., 1991). Improved left ventricular function and even more impressive improvements in survival rates have been demonstrated consistently in controlled studies. Benefit is related to the restoration of myocardial blood flow. Maximal benefit is achieved with early and sustained restoration of coronary artery patency. Patients must be assessed carefully prior to initiating treatment, especially for potential bleeding hazards,and appropriate follow-up evaluation and concomitant therapy needs to be planned. However, given the overwhelming body of data now available regarding its benefits and relative safety, thrombolysis should be considered as conventional therapy for patients with acute evolving myocardial infarction.

Animal studies of stroke have been encouraging with regard to arterial recanalization and safety (reviewed in Brott, 1991; Levine, et al., 1992). Arterial recanalization has been demonstrated in patients with ischemic stroke following the administration of any one of several thrombolytic drugs. Placebo-controlled trials have not been completed, and so clinical benefit has not been established. Even though the development of brain hemorrhage has been an infrequent complication, the very high morbidity and mortality have been worrisome. Ironically, thrombolytic therapy holds promise for treatment of subarachnoid hemorrhage and perhaps also for spontaneous intracerebral hemorrhage. Human studies have been limited, but complications have been modest, and clinical outcomes have been encouraging.

In still yet another preferred embodiment, a polypeptide encoded by an encoding region has the ability to catalyze the conversion of a pro-drug to a drug or to sensitize a cell to a therapeutic agent. By way of example, cells manipulated to contain a herpes simplex virus (HSV) gene for thymidine kinase (tk) and to express HSV-tk become sensitive to the action of the antiviral agent ganciclovir (GCV) (Culver et al., 1992). By way of further example, cells manipulated to contain a gene for bacterial cytosine deaminase and to express that enzyme can catalyze the conversion of inactive, non-toxic 5'-fluorocytosine to the active cytotoxin 5-fluorouracil (Culver et al., 1992).

Thus, a preferred polypeptide that has the ability to catalyze the conversion of a pro-drug to a drug or to sensitize a cell to a therapeutic agent is herpes simplex virus thymidine kinase or a cytosine deaminase.

A further preferred polypeptide encoded by an encoding region is a surface antigen that is a gene product of a major histocompatibility complex (MHC). As is well known in the art, MHC represents a set of linked genetic loci involved in regulating the immune response. MHC gene products occur on cell surfaces where they act as antigenic markers for distinguishing self from non-self. Typically, MHC gene products are classified as being of a class I or Class II depending upon their function. MHCs from different animals have been given different and corresponding designations. By way of example, human MHC gene products are designated by the prefix HL; mouse MHC gene products are designated by the prefix H-2; rat MHC gene products are designated by the prefix RT1 and chimpanzee MHC gene products are designated by the prefix ChLA.

Exemplary and preferred human MHC gene products are class I antigens HLA-A, HLA-B and HLA-D and class II antigens HLA-Dr and HLA-Dc.

b. More than one polypeptide

In another aspect, an encoding region of a DNA molecule of the present invention encodes the whole or a portion of more than one polypeptide. Preferably, those polypeptides are transcription factors.

A transcription factor is a regulatory protein that binds to a specific DNA sequence (e.g., promoters and enhancers) and regulates transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

In accordance with such an embodiment, an encoding region comprises:

(a) a first encoding sequence that encodes a DNA binding domain of a first transcription factor;

(b) a second encoding sequence that encodes an activation or repression domain of a second transcription factor;

(c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (d) a transcription-terminating region that is operatively linked to any of the first, second or third encoding sequences such that the transcription-terminating region is located 3' to all of the first, second and third encoding sequences.

As used herein, the phrase "operatively linked in frame" means that encoding sequences are connected to one another such that an open reading frame is maintained between those sequences. Means for linking DNA encoding sequences in frame are well known in the art.

DNA binding domains of transcription factors are well known in the art. Exemplary transcription factors known to contain a DNA binding domain are the GAL4, c-fos, c-Jun, lac1, trpR, CAP, TFIID, CTF, Sp1, HSTF and NF-κB proteins. Preferably, a DNA binding domain is derived from the GAL4 protein.

The GAL4 protein is a transcription factor of yeast comprising 881 amino acid residues. The yeast protein GAL4 activates transcription of genes required for catabolism of galactose and melibiose. GAL4 comprises numerous discrete domains including a DNA binding domain (Marmorstein et al., 1992).

The DNA sequences recognized by GAL4 are 17 base pairs (bp) in length, and each site binds a dimer of the protein. Four such sites, similar but not identical in sequence, are found in the upstream activating sequence (UAS$_G$) that mediates GAL4 activation of the GAL1 and GAL10 genes, for example (Marmorstein et al., 1992).

Functions have been assigned to various parts of the 881-amino-acid GAL4 protein, including DNA binding (residues 1–65) and dimerization (residues 65–94). In addition, three acidic activating regions have been identified (residues 94–106; 148–196; 768–881) as has a region near the carboxyl terminus that binds the inhibitory protein GAL80 (Marmorstein et al., 1992).

The DNA-binding region of GAL4 has six cysteine residues, conserved among a set of homologous proteins, that coordinate two $Zn^{2+}$ ions in a bimetal-thiolate cluster. Residues 10–40, which form the metal binding domain, are a compact globular unit. Residues 1–9 and residues C-terminal to 41 are disordered (Marmorstein et al., 1992).

The protein fragment binds to its DNA site as a symmetrical dimer. Each subunit folds into three distinct modules: a compact, metal-binding domain (residues 8–40), an extended linker (residues 41–49), and an α-helical dimerization element (residues 50–64). The metal-binding domain contacts three DNA base pairs in the major groove, and is therefore referred to as a recognition module (Marmorstein et al., 1992).

The recognition module is held together by two metal ions, tetrahedrally coordinated by the six cysteines. The recognition module of GAL4 defines a class in the group of DNA-binding domains that have $Zn^{2+}$ as a structural element.

Residues 50–64 form an amphipathic α-helix. The complete GAL4 molecule contains additional residues between 65 and 100 that contribute to dimer interactions and maintain the protein as a dimer even when it is not bound to DNA. The amino-acid sequence of GAL4 is consistent with a coiled-coil that may continue for one heptad repeat beyond the C terminus of GAL4 (1–65). Moreover, residues 79–99 include three potentially α-helical heptad sequences. The intervening segment (residues 72–78) contains a proline. The full dimerization element of GAL4 could therefore share some structural features with the 'helix-loop-helix' transcription factors.

At least eleven other fungal DNA-binding proteins are known to contain repeated $CX_2CX_6C$ sequences like those found in the GAL4 recognition module: LAC9, PPR1, QA-1F, QUTA1, ARGRII, HAP1, MAL63, LEU3, PUT3, and AMDR. In most of them, the 'loop' between the third and fourth cysteines is six residues long, but it is one residue shorter in MAL63, PDR1, PUT3 and AMDR, and several residues longer in LEU3. GAL4 residues 15–20, which are in closest proximity to DNA in the complex, are highly conserved in these homologues. Arg 15 and Lys 20, which form phosphate salt links that anchor the first helix of the recognition module to DNA, are conserved in all but AMDR, which has His and Arg at these positions, respectively. Residue 19 is usually hydrophobic, and residue 17 is basic, except in QA-1F and LEU3. Lys 18, which makes base-specific contacts in the GAL4 complex, is conserved in all but three cases. In two of the exceptions (QA-1F and MAL63) it is Arg; in the other (PUT3), it is His. These conservations suggest that the recognition modules of these GAL4 homologues all approach DNA in a similar way (Marmorstein et al., 1992).

There are symmetrically disposed CCG sequences in known sites for LAC9, PPR1, LEU3 and PUT3. Characteristic heptad sequences suggest that several of the homologue (LAC9, QA-1F, QUTA1, PPR1) contain coiled-coil dimerization elements similar to the one in GAL4. In others such as ARGRII, HAP1, and LEU3, no obvious heptad sequences occur in the 60 residues immediately C-terminal to the recognition modules. In LEU3, the heptads lie one residue closer to the recognition module than in GAL4; in HAP1, they appear to be displaced toward the C terminus by seven residues. Some heterogeneity of dimerization structures and of linker lengths is implied by these observations (Marmorstein et al., 1992).

The closest relatives of GAL4 are LAC9, which carries out the same function in *K. lactics*, and PPR1, which regulates pyrimidine biosynthesis in *S. cerevisiae*. GAL4 and LAC9 bind to the same DNA sites; PPR1 recognizes sites with the CCG triplet separated by six, rather than 11, base pairs. GAL4 and LAC9 have similar amino-acid sequences in their linker and dimerization segments; the linker and dimerization elements of PPR1 bear no sequence similarity to those of GAL4, aside from the rough characteristics of their heptad regions (Marmorstein et al., 1992).

In a preferred embodiment, therefore, a first encoding sequence of a DNA molecule of the present invention encodes a DNA binding domain of GAL4. Preferably, that binding domain comprises amino acid residue sequences 1 to about 147 of GAL4, which numerical designations refer to amino acid residue sequences numbered consecutively beginning at the amino terminus. Thus, a first encoding sequence comprises about 444 nucleotide base pairs of the GAL4 gene, which base pairs encode amino acid residue sequences 1 to 147 of GAL4.

In another preferred embodiment, a first encoding sequence of a DNA molecule of the present invention encodes a DNA binding domain of GALA that comprises amino acid residue sequences 1 to about 65 of GAL4, which numerical designations refer to amino acid residue sequences numbered consecutively beginning at the amino terminus. Thus, a first encoding sequence comprises about 198 nucleotide base pairs of the GAL4 gene, which base pairs encode amino acid residues 1 to 65 of GAL4.

Transcription factors having activation or repression domains are well known in the art. Exemplary transcription factors having activation domains are GAL4, c-Jun, viral protein VP-16, and nuclear factor NF-κB.

As set forth above, GAL4, a protein of 881 amino acid residues, activates transcription of factors involved in carbohydrate metabolism of yeast. There are likely two or three acidic activation domains in the GAL4 protein. Those activation domains comprise (1) amino acid residues 94 to 106, (2) amino acid residues 148 to 196, and (3) amino acid residues 768 to 881, where amino acid residues are numbered consecutively beginning at the amino terminus (Marmorstein et al., 1992).

In one embodiment, a second encoding sequence encodes an activation domain of GAL4. Such an encoding sequence comprises nucleotide base sequences of about, 69, 147 and 342 base pairs, respectively that encode the activation domains set forth above.

C-Jun is a major form of the 40 to 44 kD AP-1 transcription factor. Several regulatory and DNA binding domains exist within the Jun protein. Close to the DNA binding domain is a region designated as $A_2$, which is required to activate transcription (Lewin, 1991). $A_1$, an additional transcriptional activation domain is found near the N terminus adjacent to a region termed Delta (Δ) which is proposed to bind a cellular protein that inhibits the transcriptional activating properties of Jun (Baichwal, 1990 and Baichwal, 1991. Jun transcriptional activity can be conferred through either or both activation domains $A_1$ and $A_2$.

Increased Jun binding to AP-1 sequences following irradiation suggest that Jun protein is modified following irradiation. Taken together with the recent findings that protein kinase C (PKC) is activated following irradiation of cells and that PKC depletion suppress c-Jun induction by irradiation (Hallahan, 1992), it is likely that irradiation activates Jun through MAP-K modification of the $A_1$ domain (Binetruy, 1991 and Pulverer, 1991).

The ability of a Jun activation domain to stimulate transcription was demonstrated in studies of cells transformed or transfected with DNA molecules comprising such domains. HeLa and RIT-3 cells were transfected with two plasmids. Plasmid pSG-Jun5-253 contained the SV40 promoter (not transcriptionally responsive to radiation) upstream of an encoding region that encoded a chimeric protein (GAL4-Jun) comprising a sequence for Δ, $A_1$, and $A_2$ (Baichwal, 1990) and the DNA binding domain of the yeast GAL4 gene (the DNA binding domain of Jun was replaced with the DNA binding domain of the GAL4 gene, Baichwal, 1990). A second plasmid, G5BCAT was constructed to contain the DNA sequence that binds Gal4 protein placed 5' of the E1b TATA box and upstream of the CAT reporter gene (Baichwal, 1990).

Transcriptional activation of the activation domain of Jun by irradiation of transfected cells stimulated transcription and expression of the chimeric Gal-Jun protein, which protein bound to the Gal4 binding sequence and initiated transcription and expression of CAT. Irradiation of RIT-3 cells transfected with G5BCAT alone demonstrated no increase in CAT activity. Similar results were obtained in HeLa cells which contain the Jun inhibitor.

However, Hep G2 cells (which do not contain the Jun inhibitor; Baichwal, 1990) transfected with pSG-Jun5-235 and G5BCAT demonstrated no x-ray-induced activation of the Gal4-Jun chimeric protein. These data suggest that the Gal-Jun chimeric protein is activated following irradiation resulting in DNA binding to accelerate transcription of CAT.

Because X-ray induced c-Jun gene expression is attenuated when PKC is depleted or inhibited, the PKC inhibitor H7 was added to RIT-3 cells transfected with pSG-Jun5-235 and G5BCAT. H7 treatment abrogated the x-ray induced increase in CAT activity suggesting that irradiation induced PKC activation is required for gene expression (Hallahan, 1991a; Hallahan, 1991b). These data suggest that dissociation from the Jun inhibitor may be one mechanism of regulating radiation-mediated transcription.

In yet another aspect, a DNA molecule of the present invention comprises a binding region that is capable of binding a DNA binding domain of a transcription factor, which binding region is operatively linked to a minimal promoter that is operatively linked to an encoding region that encodes a polypeptide, which encoding region is operatively linked to a transcription-terminating region.

Preferably, a binding region is capable of binding the DNA binding domain of the first transcription factor set forth above. By way of example, where the binding domain is a Gal4 binding domain, a binding region of a DNA molecule binds that Gal4 binding domain. A binding region is operatively linked to a minimal promoter (e.g., a TATA box) that is operatively linked to an encoding region that encodes a polypeptide. An exemplary preferred DNA molecule comprising a binding region, minimal promoter and encoding region is plasmid pG5BCAT. Plasmid pG5BCAT comprises a binding region that binds the DNA binding domain of Gal4 (amino acid residues 1–147) operatively linked to an E1b TATA box that is operatively linked to CAT gene (See Example vv hereinafter).

In a preferred embodiment, an activation domain is an activation domain of viral protein VP-16 or nuclear factor NK-fB.

Viral protein VP-16 is a 65 kD polypeptide of about 490 amino acid residues that is expressed during the immediate early phase of herpes simplex viral infection and activates transcription and subsequent expression of infected cell proteins (ICP) such as ICP4 (Trienzenberg et al., 1988).

The activation domain of VP-16 comprises an amino acid residue sequence of about 78 amino acid residues located at the carboxy-terminus of VP16 (amino acid residues 413 to 490 as numbered from the amino-terminus). The activation domain of VP16 is further likely centered in a 61 amino acid residue sequence located from about residue 429 to about residue 456 (Trienzenberg et al., 1988).

Thus, in a preferred embodiment, a second encoding sequence encodes amino acid residue sequences from about residue number 413 to about residue number 490 of VP16 and, more preferably from about residue number 429 to about residue number 456 of VP16.

Nuclear factor NF-κB is a transcription factor. The activation domain of NF-κB comprises amino acid residue sequences from about residue position 414 to about residue position 515, numbered from the amino-terminus. Thus, a second encoding sequence preferably comprises nucleotide base pairs that encode amino acid residues from about residue position 414 to about residue position 515 of NF-κB (Ballard, 1992).

c. Nuclear localization signal

At least one of the encoding sequences contains a nuclear localization signal. Such a signal permits the encoded transcription factor to enter the nucleus and interact with DNA in the nucleus. Preferably, such a nuclear localization signal is contained in the first or second encoding sequence. Where a nuclear localization signal is not present in a first or second encoding sequence such a signal is contained in a third encoding sequence.

Nuclear localization signals are well known in the art. An exemplary and preferred such signal is derived from Simian Virus 40 (SV40) large T antigen. In a preferred embodiment, a SV40 nuclear localization signal comprises an amino acid residue sequence of from about 7 to about 15 amino acid residues around a lysine (Lys) residue at position 128 of SV40 large T antigen (Kalderon et al. 1984). In a more preferred embodiment a nuclear localization signal comprises the amino acid residue sequence of SV40 extending from about residue position 126 to about residue position 132.

d. Transcription-terminating region

RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Transcription-terminating regions are well known in the art. A preferred transcription-terminating region used in a DNA molecule of the present invention comprises nucleotides 1533 to about 2157 of the human growth hormone (Seeburg, 1982).

3. Preparation of a DNA Molecule

A DNA molecule of the present invention is prepared in accordance with standard techniques well known to a skilled worker in the art. First, DNA fragments containing the various regions of a desired DNA molecule are prepared or isolated. Those regions are then ligated to form a DNA molecule of this invention. Means for synthesizing, isolating and ligating DNA fragments are well known in the art.

DNA sequences of up to about 200 base pairs can be prepared using well known solid phase synthetic techniques. Thus, by way of example, where a radiation responsive enhancer-promoter is a CArG domain of an Egr-1 promoter, one or more of that domain can be synthetically prepared.

Where a desired DNA sequence is of about 200 or more nucleotides, that sequence is typically obtained from tissues, cells or commercially available constructs (e.g. vectors or plasmids) known to contain that desired sequence.

By way of example, a cDNA clone of Egr-1 has been isolated and sequenced from mouse liver (Tsai-Morris, 1988). A cDNA of c-Jun has been isolated and sequenced from rat (Hatori, 1988 and Unlap, 1992). Sources known to contain encoding DNA regions that encode specific polypeptides are well known in the art. Table 1 below summarizes sources known to contain encoding DNA sequences for exemplary polypeptides.

TABLE 1

| Polypeptide | Source of Encoding DNA |
|---|---|
| TNF | CETUS |
| ricin | CETUS |
| p53 | Dr. Vogelstein; Johns Hopkins University |
| MnSOD | Genentech |
| Pseudomonas exotoxin | Dr. Steve Lory, Univ. of Washington |

Where a DNA fragment is obtained from a cell or other organism, total DNA is extracted from that organism or cell and fragmented using restriction enzymes. The choice of what restriction enzyme or enzymes to use is dependent upon the desired DNA sequence being obtained. Particular DNA sequences of interest are then isolated, identified and purified using standard techniques well known in the art. If needed, an encoding DNA sequence can be amplified prior to isolation. A preferred means of amplifying a DNA sequence of interest is the polymerase chain reaction.

A wide variety and number of DNA molecules comprising a radiation responsive enhancer-promoter and an encoding region have been prepared (See Examples 1–6, hereinafter). Table 2, below, summarizes the composition of exemplary such DNA molecules.

TABLE 2

| Plasmid Designation | Enhancer-Promoter | Encoding Region |
|---|---|---|
| pE425-TNF | CArG domain of Egr-1 | TNF |
| pE425-CAT | CArG domain of Egr-1 | CAT |
| pE425-p53 | CArG domain of Egr-1 | p53 |
| pE425-raf 301-1 | CArG domain of Egr-1 | raf 301-1 |
| pE425-MnSOD | CArG domain of Egr-1 | MnSOD |
| pE425-Gal4/VP16 | CArG domain of Egr-1 | Gal4/VP16 |
| c-Jun-CAT | c-Jun promoter | CAT |
| AP-1CAT | AP-1 | CAT | a. pE425-TNF

Plasmid pE425-TNF comprises nucleotide bases from nucleotide position −425 to nucleotide position +65 (relative to the transcription start site) of the Egr-1 gene operatively linked to an encoding region that encodes TNF-α. pE425-TNF was constructed from plasmids pE-TNF, which contains TNF cDNA, and plasmid pE425-CAT, which contains the Egr-1 segment, a transcription-terminating region and a polyadenylation segment from CAT.

pE-TNF was digested with the restriction enzyme Pst I to yield a 1.1 kilobase (kb) fragment containing TNF cDNA. pE425-CAT was digested with the restriction enzyme Hind m to yield a 3.3 kb fragment containing the CAT gene and a 3.2 kb segment containing the Egr-1 fragment and the polyadenylation signal from CAT. The 1.1 kb fragment from pE-TNF and the 3.2 kb fragment from pE425-CAT were blunt ended at the 3' overhang with T4 DNA polymerase and at the 5' overhang with Klenow using standard procedures well known in the art.

The resulting pE425 and TNF cDNA were blunt-end ligated using T4 DNA ligase and T4 RNA ligase using standard procedures well known in the art to form pE425-TNF. Digestion of pE425-TNF with BamH1 and Hind II yielded 1.4 kb and 4.5 kb segments of the sense construct and a 0.9 kb segment of the antisense construct indicating the sense orientation of the plasmid.

Plasmid pE425-CAT was prepared from an about 491 base pair fragment of the Egr-1 promoter, which fragment is located from nucleotide base −425 to nucleotide base +65 relative to the transcriptional start site and plasmid pCATm (Gius et al. 1990).

The 491 base pair fragment of Egr-1 was obtained from plasmid p2.4, which contained a 2.4 kb fragment of the 5' flanking sequence of the Egr-1 gene (Tsai-Morris, 1988). Briefly, Balb/c 3T3 liver DNA was used to construct a ΔFix genomic library using a well known partial fill-in cloning procedure. About 100,000 unamplified clones in E.coli strain JC7623 (rec B, rec C, sbc B; Winas et al., 1985) were screened with a $^{32}$P-labeled Egr-1 plasmid OC 3.1 (Sukhatme et al., 1988) that contained a full length 3.1 kb cDNA insert. Membranes (GeneScreenPlus, New England Nuclear) were hybridized for about 16 hours at about 65° C.

in 1 percent SDS, 10 percent dextran sulfate and 1M NaCl. The filters were washed to a final stringency of 65° C. in 0.2×SSC. Autoradiaographs were prepared by exposing the filters for about 18 hours at −70° C. with an intensifying screen. A single clone, designated mgEgr-1.1 was obtained, which clone hybridized to the extreme 5' 120 bp EcoRI-ApaI fragment from plasmid OC 3.1.

A 2.4 kb PvuII-PvuII fragment and a 6.6 kb XbaI-XbaI fragment derived from mgEgr-1.1 were subcloned into the SmaI and XbaI sites of pUC13 and pUC18 (Promega Corp. Madison, Wis.), respectively, to form plasmids p2.4 and p6.6 respectively.

An about 1206 base pair fragment (nucleotide base position −957 to nucleotide base position +248 relative to the transcription start site) was obtained from plasmid p2.4 to form plasmid pEgr-1 P1.2. A deletion mutant was constructed from pEgr-1 P1.2 using oligomers and polymerase chain reaction to form the 491 base pair fragment extending from nucleotide base position −425 to nucleotide base position +65.

Plasmid pCAT3m was obtained from Dr. Laimonis A. Laimins, Howard Hughes Medical Institute Research Laboratories, University of Chicago, Chicago, Ill.). Plasmid pE-TNF was prepared in accordance with the procedure of Wong (Wong, 1985).

b. pE425-p53

Plasmid pE425-p53 comprises an about 491 base pair fragment of the Egr-1 promoter operatively linked to an encoding region for the tumor suppressing factor p53. pE425-p53 was constructed from a plasmid (pC53SN3; Diller, 1990) that contains p53 cDNA, and plasmid pE425-CAT, which contains the Egr-1 segment and a transcription-terminating region, the polyadenylation segment from CAT. Plasmid pE425-CAT was prepared as described above.

c. pE425-raf 301-1

Plasmid pE425-raf 301-1 comprises an about 491 base pair fragment of the Egr-1 promoter operatively linked to an encoding region for a serine/threonine-specific protein kinase product of-an oncogene from a 3611 murine sarcoma cell. pE425-raf 301-1 was constructed from plasmids pMN301-1, which contains the raf dominant negative (Kolch, 1991), and pE425-CAT, which contains the Egr-1 segment and a transcription-terminating region, the polyadenylation segment from CAT.

d. pE425-MnSOD

Plasmid pE425-MnSOD comprises an about 491 base pair fragment of the Egr-1 promoter operatively linked to an encoding region for the free-radical scavenger manganese superoxide dismutase (MnSOD). pE425-MnSOD was constructed from a plasmid nMnSOD #0664 (Genentech) (Wong, 1989) which contains MnSOD cDNA and pE425-CAT, which contains the Egr-1 segment and a transcription-terminating region, the polyadenylation segment from CAT.

e. G5-TNF

Plasmid G5-TNF comprises the DNA binding domain of the yeast GAL4 gene and the E1b minimal promoter TATA box operatively linked to an encoding region that encodes TNF-α. pG5-TNF was constructed from plasmid G5BCAT and plasmid pE-TNF.

Plasmid G5BCAT, which contains the DNA sequence which binds Gal4 protein placed 5' of the E1b TATA box upstream of the CAT reporter gene (Baichwal, 1990). The G5BCAT plasmid was digested with the EcoR1 restriction enzyme. The large fragment was isolated and blunt ended at the 3' overhang using T4 DNA polymerase and at the 5' overhang with Klenow. This digestion removes the minimal promoter but retains the poly-A end.

TNF cDNA was removed from the pE4 plasmid using the Pst I restriction enzyme and the 1.1 kb fragment containing TNF cDNA was isolated and blunt ended at the 3' overhand using T4 DNA polymerase and at the 5' overhang with Klenow.

The resulting G5B- and TNF cDNA were blunt-end ligated using the T4DNA ligase and T4 RNA ligase. The resulting G5-TNF plasmid underwent restriction enzyme mapping and DNA sequencing to assure the sense orientation of TNF. Plasmid G5BCAT was prepared by the method of Baichwal (Baichwal, et al., 1990). Plasmid pE-TNF was prepared as set forth above.

f. c-jun CAT

Plasmid c-Jun-CAT comprises an about 1100 base pair fragment of the c-Jun promoter operatively linked to an encoding region for CAT. Plasmid c-Jun-CAT was constructed from plasmid h-jun-CAT in accordance with the procedure of Angel (Angel, 1988).

g. pE25-Pseudomonas exotoxin

A plasmid comprising a CAr6 domain of an Egr-1 promoter and an encoding region that encodes Pseudomonas exotoxin was prepared from plasmid PE425 and plasmid pMS150A (Lory, 1988), which contains the Pseudomonas exotoxin encoding region.

h. Other constructs

Other DNA molecules of the present invention are made using techniques similar to those set forth above. Specific examples of the preparation of other DNA molecules can be found in Examples 1–6 hereinafter.

B. Pharmaceutical Composition

In another aspect, the present invention contemplates a pharmaceutical composition comprising a therapeutically effective amount of at least one DNA molecule of the present invention and a physiologically acceptable carrier.

A therapeutically effective amount of a DNA molecule that is combined with a carrier to produce a single dosage form varies depending upon the host treated and the particular mode of administration.

As is well known in the art, a specific dose level for any particular patient depends upon a variety of factors including the activity of the specific compound employed, the age, body weight, general health, sex, diet, time of administration, route of administration, rate of excretion, drug combination, and the severity of the particular disease undergoing therapy.

A composition of the present invention is typically administered orally or parenterally in dosage unit formulations containing standard, well known nontoxic physiologically acceptable carriers, adjuvants, and vehicles as desired. The term parenteral as used herein includes subcutaneous injections, intravenous, intramuscular, intraarterial injection, or infusion techniques.

Injectable preparations, for example, sterile injectable aqueous or oleaginous suspensions are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

A DNA molecule of the present invention can also be complexed with a poly(L-Lysine)(PLL)-protein conjugate such as a transferrin-PLL conjugate or an asialoorosomucoid-PLL conjugate.

Liquid dosage forms for oral administration include pharmaceutically acceptable emulsions, syrups, solutions, suspensions, and elixirs containing inert diluents commonly used in the art, such as water. Such compositions can also comprise adjuvants, such as wetting agents, emulsifying and suspending agents, and sweetening, flavoring, and perfuming agents.

C. Transformed or Transfected and Transgenic Cells

In another aspect, the present invention provides a cell transformed or transfected with one or more DNA molecules of the present invention as well as transgenic cells derived from those transformed or transfected cells. Means of transforming or transfecting cells with exogenous DNA molecules are well known in the art.

A DNA molecule is introduced into a cell using standard transformation or transfection techniques well known in the art such as calcium-phosphate- or DEAE-dextran-mediated transfection, protoblast fusion, electroporation, liposomes and direct microinjection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transferred to the nucleus. Depending on the cell type, up to 20% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that carry integrated copies of the foreign DNA, which are usually arranged in head-to-tail tandem arrays.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transferred to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandomly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transformation involves encapsulation of DNA and RNA within liposomes, followed by fusion of the liposomes with the cell membrane. In addition, DNA that is coated with a synthetic cationic lipid can be introduced into cells by fusion.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

D. Process of Regulating Expression

In another aspect, the present invention contemplates a process of regulating the expression of a polypeptide. Polypeptide expression is regulated by stimulating or inhibiting transcription of an encoding region that encodes that polypeptide. In accordance with one embodiment, a process of regulating polypeptide expression comprises the steps of:

(a) operatively linking a radiation responsive enhancer-promoter to an encoding region that encodes that polypeptide, which encoding region is operatively linked to a transcription-terminating region to form a DNA molecule; and (b) exposing the DNA molecule to an effective expression-inducing dose of ionizing radiation.

A DNA molecule used with such a method is a DNA molecule of the present invention as set forth above.

As used herein, the phrase "effective expression-inducing dose of ionizing radiation" means that dose of ionizing radiation needed to stimulate or turn on a radiation responsive enhancer-promoter of the present invention. The amount of ionizing radiation needed in a given cell depends inter alia upon the nature of that cell. Typically, an effective expression-inducing dose is less than a dose of ionizing radiation that causes cell damage or death directly. Means for determining an effective expression inducing amount are well known in the art.

In a preferred embodiment an effective expression inducing amount is from about 2 to about 20 Gray (Gy) administered at a rate of from about 0.5 to about 2 Gy/minute. Even more preferably, an effective expression inducing amount of ionizing radiation is from about 5 to about 15 Gy.

As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

Cells containing a DNA molecule of the present invention encoding a particular polypeptide express that polypeptide when exposed to ionizing radiation.

By way of example, treatment of cells transfected with plasmid pEgr-1P1.2 with ionizing radiation was associated with a 4.1-fold increase in CAT activity as compared to transfected but unirradiated cells. Plasmid pEgr-1 P1.2 comprises a radiation responsive enhancer-promoter (the Egr-1 promoter region extending from position −957 upstream to the transcription start site to position +248) operatively linked to the CAT reporter gene. Indeed, irradiation of pE425-CAT transfected cells was associated with a 3.6-fold induction of CAT activity compared to that in non-irradiated cells transfected with this construct.

A series of deleted Egr-1 promoter constructs was next used to further define the x-ray responsive elements in pE425-CAT. Sequential deletion of the three distal CArGs progressively decreased CAT activity. Plasmid pE395-CAT (first CArG deleted) conferred x-ray inducibility to a lesser extent than pE425-CAT. Deletion of the first and second CArG domains (pE359-CAT) resulted in further decreases in CAT activity, while deletion of the first three CArG domains (pE342-CAT)) was associated with minimal increases in CAT activity.

Other studies were performed with fragments of the Egr-1 promoter linked to HSV-TK and the CAT gene. There was no detectable inducibility of pTK35CAT (not containing any CArG domains of an Egr-1 promoter) by x-rays. In contrast, cells transfected with plasmid pE425/250TK (containing the four distal Egr-1 CArG domains) were responsive to x-ray treatment. The region of the Egr-1 promoter extending from nucleotide positions −395 to −250, which region does not include the first CArG domain, was also functional in conferring x-ray inducibility to the heterologous promoter, but to a lesser extent than pE425/250TK. X-ray inducibility of CAT expression was also observed in cells transfected with a plasmid comprising only one CArG domain.

By way of further example, TNF-α protein expression was induced by ionizing radiation in cells transfected with plasmid pE425-TNF. SQ-20B, RIT-3 and HL-525 cells were transfected with plasmid pE425-TNF by DEAE precipitation. Transfected cells were exposed to 10 Gy of x-radiation at a rate of 1 Gy/minute. TNF-A expression was increased about 2-fold, 5-fold and 4-fold, respectively in SQ-20B, RIT-3 and HL-525 cells when compared to transfected, non-irradiated cells.

By way of still further example, CAT expression was induced by ionizing radiation in RIT-3 cells transfected with plasmid c-Jun-CAT, which plasmid comprises a 1100 base pair segment of the c-Jun promoter operatively linked to a CAT gene. Cells were cotransfected with an SV40 promoter-β galactosidase expression vector to control for transfection efficiency.

Transfectants were irradiated (10 Gy, 1 Gy/min, GE Maxitron) 40 hours after transfection. CAT was extracted 6 hours after irradiation. CAT activity increased about 3-fold following irradiation of RIT-3 cells transfected with pc-Jun-CAT. β gal expression was not affected by radiation. Ionizing radiation did not increase CAT expression in cells transfected with a plasmid comprising the minimal Jun promoter (nucleotide base position-18 to nucleotide base position +170 relative to the transcription start site) operatively linked to CAT.

The data set forth above show that ionizing radiation can be used as a trigger to regulate transcription of an encoding region in a DNA molecule of the present invention and expression of a polypeptide encoded by that region.

In an alternate embodiment, polypeptide expression is regulated by the use of two DNA molecules. One of those DNA molecules comprises a radiation responsive enhancer-promoter operatively linked to an encoding region that comprises:

(a) a first encoding sequence that encodes a DNA binding domain of a first transcription factor;

(b) a second encoding sequence that encodes an activation or repression domain of a second transcription factor;

(c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (d) a transcription-terminating region that is operatively linked to any of the first, second or third encoding sequences such that the transcription-terminating region is located 3' to all of the first, second and third encoding sequences.

A second DNA molecule comprises a binding region that is capable of binding the DNA binding domain of the first transcription factor, which binding region is operatively linked to a minimal promoter that is operatively linked to an encoding region that encodes a polypeptide, which encoding region is operatively linked to a transcription-terminating region.

A radiation responsive enhancer-promoter, a transcription factor, a binding domain of a transcription factor and an activation or repressor domain of a transcription factor are preferably those set forth above. A polypeptide encoded by an encoding region is also preferably the same as set forth above.

Cells transfected with such DNA molecules show ionizing radiation-inducible polypeptide expression.

By way of example, two plasmids were transfected into HeLa and RIT-3 cells using a calcium precipitation method. The first plasmid (pSG424) contained the SV40 promoter (not transcriptionally responsive to radiation) upstream of the coding sequence, for δ, A1, and A2 regions of the activation domain of the Jun protein, wherein the DNA binding domain of Jun was replaced with the DNA binding domain of GAL4. A second plasmid, G5BCAT contained the DNA sequence which binds Gal4 protein linked to a minimal TK promoter upstream of the CAT reporter gene.

Transfected cells were irradiated with 10 Gy of x-rays. CAT activity increased in the irradiated, transfected HeLa and RIT-3 cells as compared to transfected, non-irradiated cells.

By way of further example, irradiation induced an increase in TNF-α expression in RIT-3 cells transfected with plasmids pE425-Gal4/VP-16 and pG5-TNF. Plasmid pE425-Gal4/VP-16 comprises an about 491 base pair fragment of the Egr-1 promoter containing 6 CArG domains, which fragment is operatively linked to an encoding region comprising a first encoding sequence encoding DNA binding domain of Gal4 operatively linked in frame to a second encoding sequence encoding the activation domain of viral protein VP-16. Plasmid G5-TNF comprises a DNA segment that binds the Gal4 binding domain operatively linked to minimal promoter operatively linked to an encoding region that encodes TNF-α. RIT-3 cells were cotransfected with the pE425-Gal/VP16 and G5-TNF plasmids using lipofaction. Transfected cells were irradiated 36 hours following transfection and TNF was assayed 10 hours following irradiation. The concentration of intracellular TNF increased about 9-fold as compared to cells transfected with G5-TNF alone.

Where regulating is inhibiting, an encoding region preferably comprises:

(a) a first encoding sequence that encodes a DNA binding domain of a first transcription factor;

(b) a second encoding sequence that encodes an activation or repression domain of a second transcription factor;

(c) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and (d) a transcription-terminating region that is operatively linked to any of the first, second or third encoding sequences such that the transcription-terminating region is located 3' to all of the first, second and third encoding sequences.

Preferably the second encoding sequence encodes the repression domain of the Wilms' tumor suppressor gene WT1 or the repression domain of Egr-1. A radiation responsive enhancer-promoter and a first transcription factor are the same as set forth above.

E. Process of Inhibiting Tumor Growth

In yet another aspect, the present invention contemplates a process of inhibiting growth of a tumor comprising the steps of:

(a) delivering to the tumor a therapeutically effective amount of a DNA molecule comprising a radiation responsive enhancer-promoter operatively linked to an encoding region that encodes a polypeptide having the ability to inhibit tumor cell growth, which encoding region is operatively linked to a transcription-terminating region; and (b) exposing the tumor to an effective expression-inducing dose of ionizing radiation.

Preferably, a radiation responsive enhancer-promoter comprises a CArG domain of an Egr-1 promoter, a TNF-α promoter or a c-Jun promoter and a polypeptide having the ability to inhibit tumor cell growth is a cytokine, a dominant negative, a tumor suppressing factor or an angiogenesis inhibitor. Exemplary and preferred polypeptides are TNF-α, interleukin-4, ricin, Pseudomonas toxin, p53, the retinoblastoma gene product or the Wilms' tumor gene product.

TNF is cytotoxic to tumor cells. An interaction between TNF and radiation was found in 12 human epithelial tumor cell lines analyzed for cytotoxicity to TNF and synergistic killing by combining the two agents (Hallahan, et al., 1990; Hallahan, et al., 1989). TNF was found to have cytotoxic effects at concentrations of 10 to 1000 units/ml in ten of twelve tumor cell lines studied (Hallahan, et al., 1990; Hallahan, et al., 1989). Furthermore, synergistic or additive killing by TNF and x-rays was observed in seven of those ten cell lines.

When cells from a murine renal cell tumor were engineered to secrete large doses of interleukin-4 (IL-4) locally, they were rejected in a predominantly T cell-independent manner (Golumbek, et al., 1985). However, animals that rejected the IL-4 transfected tumors developed T cell-dependent systemic immunity to the parental tumor. This systemic immunity was tumor-specific and primarily mediated by CD8+T cells. Established parental tumors could be cured by the systemic immune response generated by injection of the genetically engineered tumors. These results provide a rationale for the use of lymphokine gene-transfected tumor cells that are activated by irradiation as a modality for cancer therapy.

Ricin is a cytotoxin that inactivates mammalian ribosomes by catalyzing the cleavage of the N-glycosidic bond of 28S rRNA (Endo & Tsurngi, 1987). This enzyme is extremely toxic when given systemically, but may be localized to tumor through the use of radiation targeting of the gene encoding ricin.

The transforming growth factor type alpha gene has been fused to modified Pseudomonas toxin gene from which the cell-recognition domain has been deleted (Chaudhary, et al., 1987). The chimeric gene has been expressed in *Escherichia coli*, and the chimeric protein, PE40-TGF-alpha, has been highly purified. PE40-TGF-alpha kills cells expressing epidermal growth factor receptors and has little activity against cells with few receptors. This chimeric protein might be useful in treating cancers that contain high numbers of epidermal growth factor receptors. The gene encoding pseudomonas toxin or its chimeric may be targeted by radiation to eliminate the potential systemic sequelae of this toxin.

Delivering is preferably injecting the DNA molecule into the tumor. Where the tumor is in a subject delivering is preferably administering the DNA molecule into the circulatory system of the subject. In a more preferred embodiment, administering comprises the steps of:

(a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a leukocyte such as a tumor infiltrating lymphocyte or a T cell or a tumor cell from the tumor being treated. Means for transforming or transfecting a cell with a DNA molecule of the present invention are set forth above.

Human lymphocytes can also be transfected with radiation-inducible plasmid constructs using existing technology including retroviral mediated gene transfer (Overell, et al., 1991; Fauser, 1991). In an exemplary embodiment, LAK cells which tend to home in on the tumor site in question with some degree of preference though as is well known, they will also distribute themselves in the body in other locations, may be used to target tumors. Indeed, one of the most important advantages of the radiation inducible system is that only those LAK cells, which are in the radiation field will be activated and will have their exogenously introduced lymphokine genes activated. Thus, for the case of LAK cells, there is no particular need for any further targeting.

Alternatively, the vehicle is a virus or an antibody that specifically infects or immunoreacts with an antigen of the tumor. Retroviruses used to deliver the constructs to the host target tissues generally are viruses in which the 3' LTR (linear transfer region) has been inactivated. That is, these are enhancerless 3'LTR's, often referred to as SIN (self-inactivating viruses) because after productive infection into the host cell, the 3'LTR is transferred to the 5' end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell, e.g., LAK cells.

For purposes of this invention, a radiation responsive enhancer-promoter which is 5' of the appropriate encoding region may be cloned into the virus using standard techniques well known in the art.

The viral constructs are delivered into a host by any method that causes the constructs to reach the cells of the target tissue, while preserving the characteristics of the construct used in this invention. By way of example, a rat glioma cell line, C6-BU-1, showed differential susceptibility to herpes simplex virus type 1 (HSV-1) and type 2 (HSV-2), namely, all the HSV-1 strains tested so far persisted in this cell line but the HSV-2 strains did not (Sakihama, et al., 1991). C6-BU-1 cells consist of subpopulations heterogeneous in susceptibility to HSV-1 which may be possibly interchangeable. Furthermore, growth of tumors produced from C6-derived cells bearing the HSV-1 tk gene, but no parental C6 cells, could be inhibited by intraperitoneal administration of ganciclovir (Ezzeddine, et al., 1991). This work demonstrated the effectiveness of the thymidine kinase expressed by the HSV-1 tk gene in sensitizing brain tumor cells to the toxic effects of nucleoside analogs. Retrovirus vectors should thus prove useful in the selective delivery of this killer gene to dividing tumor cells in the nervous system, where most endogenous cells are not dividing. Radiation will be used to enhance the specificity of delivery or activation of transcription of the tk gene only in irradiated areas.

Antibodies have been used to target and deliver DNA molecules. An N-terminal modified poly(L-lysine) (NPLL) -antibody conjugate readily forms a complex with plasmid DNA (Trubetskoy et al., 1992). A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

In a preferred embodiment exposing comprises the steps of:
a) providing a radiolabelled antibody that immunoreacts with an antigen of the tumor; and
b) delivering an effective expression inducing of the radiolabelled antibody to the tumor.

The efficacy of using antibodies to target radiotherapy has been demonstrated including the modeling of dose to tumor and normal tissue from intraperitoneal radioimmunotherapy with alpha and beta emitters[4]. This technology has been applied to in vivo experiments. Astatine-211 labeling of an antimelanoma antibody and its Fab fragment using N-succinimidyl p-astatobenzoate: comparison in vivo with the p-[125]iodobenzoyl conjugate[5].

Alternatively, a process of inhibiting growth of a tumor comprises the steps of:
a) delivering to the tumor a therapeutically effective amount of
(1) a first DNA molecule comprising a radiation responsive enhancer-promoter operatively linked to an encoding region that comprises
(i) a first encoding sequence that encodes a DNA binding domain of a first transcription factor;
(ii) a second encoding sequence that encodes an activation or repression domain of a second transcription factor;
(iii) a third encoding sequence that encodes a nuclear localization signal, whereby the first, second and third encoding sequences are operatively linked in frame to each other in any order with the proviso that the third encoding sequence need be present only if the first or second encoding sequence does not encode a nuclear localization signal; and
(iv) a transcription-terminating region that is operatively linked to any of the first, second or third encoding sequences such that the transcription-terminating region is located 3' to all of the first, second and third encoding sequences; and
(2) a second DNA molecule comprising a binding region that is capable of binding the DNA binding domain of the first transcription factor, which binding region is operatively linked to a minimal promoter that is operatively linked to an encoding region that encodes a polypeptide having tumor cell cytotoxic activity, which encoding region is operatively linked to a transcription-terminating region; and
b) exposing the cell to an effective expression-inducing dose of ionizing radiation.

Preferably, a radiation responsive enhancer-promoter comprises a CArG domain of an Egr-1 promoter or an AP-1 binding domain of a c-Jun promoter and the polypeptide having tumor cell cytotoxic activity is a cytokine, a dominant negative, a tumor suppressing factor, or an angiogenesis inhibitor as set forth above.

Delivering is preferably the same as set forth above.

TNF-α is increased after treatment with x-rays in certain human sarcoma cells. The increase in TNF-α mRNA is accompanied by the increased production of TNF-α protein. The induction of a cytotoxic protein by exposure of cells containing the TNF gene to x-rays was suspected when medium decanted from irradiated cultures of some human sarcoma cell lines was found to be cytotoxic to those cells as well as to other tumor cell lines. The level of TNF-α in the irradiated tumor cultures was elevated over that of nonirradiated cells when analyzed by the ELISA technique (Sariban, et al., 1988). Subsequent investigations showed that elevated TNF-α protein after irradiation potentiates x-ray killing of cells by an unusual previously undescribed mechanism (see Example 1).

RNA from untreated cells (control) and irradiated cells was size-fractionated and hybridized to $^{32}$P-labeled TNF-α cDNA (STSAR-13) and PE4 plasmid containing TNF-α cDNA (STSAR-48). Autoradiograms showed increased expression of TNF-α mRNA 3 hours after irradiation in cell line STSAR-13 and at 6 hours in cell line STSAR-48. These data show that TNF-α gene expression is increased after radiation.

Figure 1B:
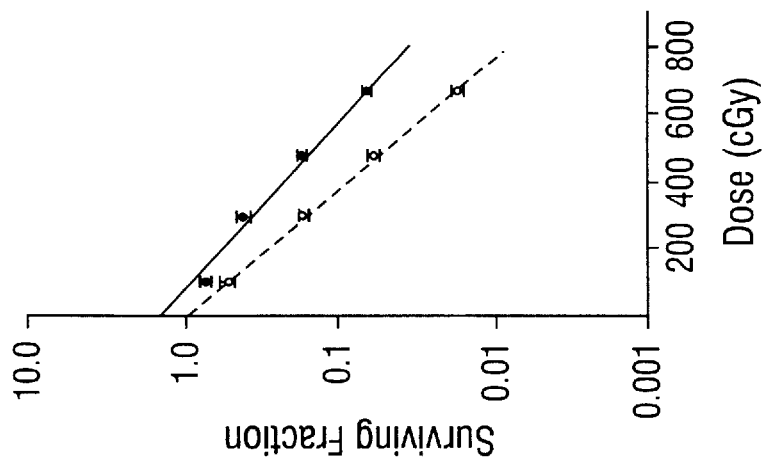
Figure 1C:
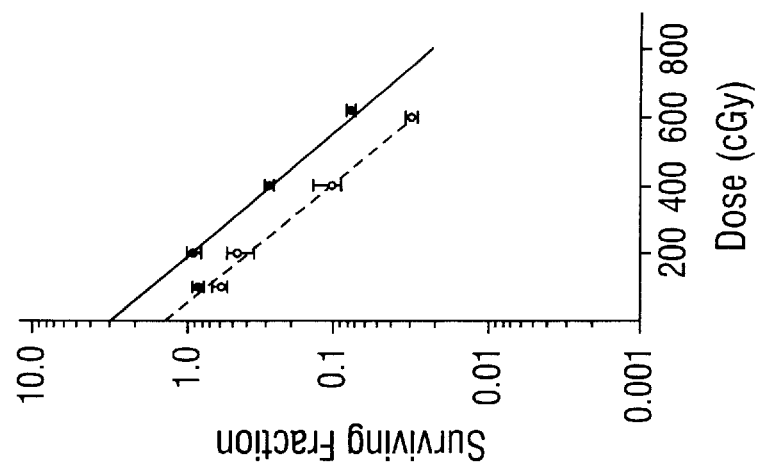

FIG. 1 exhibits the influence of TNF-α on radiation lethality of TNF-α-producing human sarcomas and TNF-α-nonproducing human tumor cells. The solid lines indicate the effects of radiation alone, and the dashed lines indicate the effects of both TNF-α and irradiation. Representative survival data for cell line STSAR-33 are shown in the graph to the left, A. The lower dashed line represents survival of cells with TNF-α at 1000 units/ml, corrected for a plating efficiency (PE) of 30%. The survival of human epithelial tumor cells (SQ-20B) irradiated with TNF-α (10 units/ml and 1000 units/ml) is shown in the middle graph, B. Survival data for SQ-20B show an additive effect of TNF-α (1000 units/ml). Survivals with TNF-α are corrected for 85% killing with TNF-α alone. Radiation survival data for HNSCC-68 is shown in the graph to the right, C. A nonlethal dose of TNF-α (10 units/ml) was added 24 hr before irradiation.

As can be seen from these results and from information discussed in Example 1, the tumor necrosis factor α is increased after treatment with x-rays. Both mRNA and TNF-α proteins were increased.

Although DNA-damaging agents other than ionizing radiation have been observed to induce expression of variety of prokaryotic and mammalian genes, the TNF-α gene is the first mammalian gene found to have increased expression after exposure to ionizing radiation. This gene is not categorized as a DNA repair gene.

A DNA molecule of the present invention has uses other than inhibition of tumor growth. Exemplary such uses are summarized below in Table 3.

TABLE 3

| Use | Encoded Polypeptide | Application to Disease |
| --- | --- | --- |
| Kill tumor cells | Toxins<br>TNF<br>Growth Factors<br>(IL-1-6, PDGF,FGF) | Solid &<br>Hematologic<br>Malignancies |
| Protect normal tissues from radiation and other cytotoxins during cancer therapy | Lymphokines GCSF<br>CMCSF<br>Erythropoietin<br>Aplastic Anemic | Solid &<br>Hematologic<br>Malignancies |
| Inhibit Metastasis | NM23 | Cancer Metastasis |
| Tumor Suppressor Gene Products | Rb p53 | Prevention of Malignancy |

TABLE 3-continued

| Use | Encoded Polypeptide | Application to Disease |
|---|---|---|
| Radiosensitization Chemosensitization (enhance routine treatment effects) | TNF | Following Standard Radio therapy and Chemotherapy Solid & Hematologic Malignancies |
| Correct Defects in Clotting Factors | Factor 8 | Clotting Disorders |
| Introduce Anticlotting Factors | Streptokinase Urokinase | Myocardial Infarction CNS Thrombosis, Pheripheral Thrombosis |
| Correct Defects Characterizing Hemoglobinopathy | Normal Hemoglobin | Sickle Cell Anemia |
| Correct Deficiencies Leading to Neurodegenerative Disease | Nerve Growth Factor | Alzheimer's Disease |
| Provide Treatment Component for Diabetes | Insulin | Diabetes |
| Disease of DNA Repair Abnormalities | ERCC-1, XRCC-1 | Ataxia Telangiectasia Xeroderma Pigmentosum |

The following examples illustrate particular embodiments of the present invention and are not limiting of the specification and claims in any way.

EXAMPLE 1

Increased Tumor Necrosis Factor α mRNA After Cellular Exposure to Ionizing Radiation A. Protein Products To investigate TNF-α protein production after x-irradiation, the levels of TNF-α in the medium of human tumor cell lines and fibroblasts were quantified by the ELISA technique (Sariban, et al., 1988) before and after exposure to 500-cGy x-rays. Five of 13 human bone and soft tissue sarcoma cell lines (STSAR-5, -13, -33, -43, and -48) released TNF-α into the medium after irradiation, whereas TNF-α levels were not elevated in supernatant from normal human fibroblast cell lines (GM-1522 and NHF-235) and four human epithelial tumor cell lines (HN-SCC-68, SCC-61, SCC-25, and SQ-20B) after exposure to radiation. The assay accurately measures TNF-α levels between 0.1 and 2.0 units per ml ($2.3 \times 10^6$ units/mg) (Saribon, et al., 1988). Tumor cell line STSAR-13 produced undetectable amounts of TNF-α before x-irradiation and 0.35 units/ml after x-ray exposure. Cell lines STSAR-5 and -33 responded to x-irradiation with increases in TNF-α concentrations of >5- to 10-fold; however quantities above 2 units/ml exceeded the range of the assay (Saribon, et al., 1988). Cell lines STSAR-43 and -48 demonstrated increases in TNF-α of 1.5- to 3-fold (Table 4, below). TNF-α protein in the medium was first elevated at 20 hr after x-ray treatment, reached maximal levels at 3 days, and remained elevated beyond 5 days. Furthermore, supernatant from irradiated, but not control STSAR-33, was cytotoxic to TNF-α-sensitive cell line SQ-20B.

TABLE 4

| | | TNF-α level (units/ml) | |
|---|---|---|---|
| Cell Line | Origin | Control | X-ray |
| STSAR-5 | MFH | 0.4 | >2.0 |
| STSAR-13 | Liposarcoma | 0.0 | 0.34 |
| STSAR-33 | Ewing sarcoma | 0.17 | >2.0 |
| STSAR-43 | Osteosarcoma | 0.41 | 1.3 |
| STSAR-48 | Neurofibrosarcoma | 0.28 | 0.43 |

TNF-α levels were measured in medium from confluent cell cultures (control) and in irradiated confluent cells (x-ray). TNF-α levels increased as measured by the ELISA technique. MFH, malignant fibrous histiocytoma.

B. RNA Analysis

Increased levels of TNF-α mRNA were detected in the TNF-α-producing sarcoma cell lines after irradiation relative to unirradiated controls. For example, TNF-α transcripts were present in unirradiated STSAR-13 and -48 cell lines. TNF-α mRNA levels in cell line STSAR-13 increased by >2.5-fold as measured by densitometry 3 hr after exposure to 500 cGy and then declined to baseline levels by 6 hours. These transcripts increased at 6 hours after irradiation in cell line STSAR-48, thus indicating some heterogeneity between cell lines in terms of the kinetics of TNF-α gene expression. In contrast, irradiation had no detectable effect on 7S RNA levels or expression of the polymerase β gene.

C. Interaction Between TNF-α and X-Irradiation

To investigate the influence of TNF-α on radiation-induced cytotoxicity in TNF-α-producing cell lines, recombinant human TNF-α was added to cultures before irradiation. Recombinant human TNF-α (1000 units/ml) ($2.3 \times 10^6$ units/mg) was cytotoxic to four of five TNF-α-producing sarcomas (STSAR-5, -13, -33, and -43). The plating efficiency (PE) was reduced by 60–90% at 1000 units/ml in these lines. Radiation-survival analysis of cell line STSAR-33 was performed with TNF-α (10 units/ml). The radiosensitivity ($D_0$), defined as the reciprocal of the terminal slope of the survival curves was 80.4 cGy for cell line STSAR-33. When TNF-α was added 20 hr before irradiation, the $D_0$ was 60.4 cGy. Surviving fractions were corrected for the reduced PE with TNF-α. Thus, the interaction between TNF-α and radiation in STSAR-33 cells was synergistic (Dewey, 1979).

Sublethal concentrations of TNF-α (10 units/ml) enhanced killing by radiation in cell line STSAR-33, suggesting a radiosensitizing effect of TNF-α. The surviving fraction of cell line STSAR-5 at 100–700 cGy was lower than expected by the independent killing of TNF-α and x-rays, although the $D_0$ values were similar. Thus, the interaction between TNF-α and radiation is additive (Dewey, 1979) in STSAR-5 cells. Cell lines STSAR-13 and STSAR-43 were independently killed with x-rays and TNF-α, and no interaction was observed.

To determine the possible interactions between TNF-α and x-rays in non-TNF-α producing cells, human epithelial tumor cells (SQ-20B and HNSCC-68) were irradiated 20 hr after TNF-α was added. These cell lines do not produce TNF-α in response to ionizing radiation. TNF-α (1000 units/ml) was cytotoxic to SQ-20B and SCC-61 cells, reducing the PE by 60–80%. The $D_0$ for cell line SQ-20B is 239 cGy. With TNF-α (1000 units/ml) added 24 hr before x-rays, the $D_0$ was 130.4 cGy. Therefore, a synergistic interaction (Dewey, 1979) between TNF-α and x-rays was demonstrated in this cell line. TNF-α added after irradiation did not enhance cell killing by radiation in cell lines SQ-20B. Nonlethal concentrations of TNF-α (10 units/ml) resulted in enhanced radiation killing in cell line HNSCC-68, providing evidence that TNF-α may sensitize some epithelial as well as mesenchymal tumor cell lines to radiation.

The following specific methods were used in Example 1.

Cell Lines. Methods of establishment of human sarcoma and epithelial cell lines have been described (Weichselbaum, et al., 1986; 1988). Culture medium for epithelial tumor cells was 72.5% Dulbecco's modified Eagle's medium/22.5% Ham's nutrient mixture F-12 (DMEM/F-12 (3:1))5% fetal bovine serum (FBS), transferrin at 5 µg/ml/$10^{-10}$M cholera toxin/$1.8\times10^{-4}$M adenine, hydrocortisone at 0.4 µg/ml/$2\times10^{-11}$M triodo-L-thyronine/penicillin at 100 units/ml/streptomycin at 100 µg/ml. Culture medium for sarcoma cells was DMEM/F-12 (3:1)/20% FBS, penicillin at 100 units/ml/streptomycin at 100 µg/ml.

TNF-α Protein Assay. Human sarcoma cells were cultured as described above and grown to confluence. The medium was analyzed for TNF-α 3 days after feeding and again 1–3 days after irradiation. Thirteen established human sarcoma cell lines were irradiated with 500-centigray (cGy) x-rays with a 250-kV Maxitron generator (Weichselbaum, et al., 1988). TNF-α was measured by ELISA with two monoclonal antibodies that had distinct epitopes for TNF-α protein (Sariban, et al., 1988); the assay detects TNF-α from 0.1 to 2.0 units/ml.

RNA Isolation and RNA Blot Analysis. Total cellular RNA was isolated from cells by using the guanidine thiocyanate-lithium chloride method (Cathala, et al., 1983). RNA was size-fractionated by formaldehyde-1% agarose gel electrophoresis, transferred to nylon membranes (GeneScreenPlus, New England Nuclear), hybridized as previously described to the 1.7-kilobase (kb) BamHI fragment of the PE4 plasmid containing TNF-α cDNA (19, 23), and autoradiographed for 16 days at −85° C. with intensifying screens. Northern blots were also hybridized to 7S rRNA and β-polymerase plasmids as described (Fornace, et al., 1989). Ethidium bromide staining revealed equal amounts of RNA applied to each lane. RNA blot hybridization of TNF-α was analyzed after cellular irradiation with 500 cGy. Cells were washed with cold phosphate-buffered saline and placed in ice at each time interval. RNA was isolated at 3, 6, and 12 hr after irradiation.

X-Irradiation and TNF-α. Exponentially growing cells were irradiated by using a 250-kV x-ray generator. The colony-forming assay was used to determine cell survival (Weichselbaum, et al., 1988). The multitarget model survival curves were fit to a single-hit multitarget model ($S=1-(-e^{-D|D_0}})^y$). Concentrations of recombinant human TNF-α (10 units/ml) ($2:3\times10^6$ units/mg) and (1000 units/ml) (Asahi Chemical, New York) were added 24 hr before irradiation.

EXAMPLE 2

Increased c-Jun Expression After Exposure to Ionizing Radiation

Another embodiment of a DNA molecule derives from the c-Jun protooncogene and related genes. Ionizing radiation regulates expression of the c-Jun protooncogene, and also of related genes c-fos and Jun-B. The protein product of c-Jun contains a DNA binding region that is shared by members of a family of transcription factors. Expression level after radiation is dose dependent. The c-Jun gene encodes a component of the AP-1 protein complex and is important in early signaling events involved in various cellular functions. AP-1, the product of the protooncogene c-Jun recognizes and binds to specific DNA sequences and stimulates transcription of genes responsive to certain growth factors and phorbol esters (Bohmann, et al., 1987; Angel, et al., 1988). The product of the c-Jun protooncogene contains a highly conserved DNA binding domain shared by a family of mammalian transcription factors including Jun-B, Jun-D, c-fos, fos-B, fra-1 and the yeast GCN4 protein.

In addition to regulating expression of the c-Jun gene, c-Jun transcripts are degraded posttranscriptionally by a labile protein in irradiated cells. Posttranscriptional regulation of the gene's expression is described in Sherman, et al., 1990.

Contrary to what would be expected based on previous DNA damage and killing rates for other agents, decreasing the dose rate, for example, from 14.3 Gy/min to 0.67 Gy/min. was associated with increased induction of c-Jun transcripts.

Maximum c-Jun mRNA levels were detectable after 50 Gy of ionizing radiation. Similar kinetics of c-Jun induction were observed in irradiated human U-937 monocytic leukemia cells and in normal human AG-1522 diploid fibroblasts. Treatment of AG-1522 cells with ionizing radiation was also associated with the appearance of a minor 3.2-kb c-Jun transcript.

The following methods were used in Example 2.

Cell Culture. Human HL-60 promyclocytic leukemia cells, U-937 monocytic leukemia cells (both from American Type Culture Collection), and AG-1522 diploid foreskin fibroblasts (National Institute of Aging Cell Repository, Camden, N.J.) were grown in standard fashion. Cells were irradiated using either Philips RT 250 accelerator at 250 kV, 14 mA equipped with a 0.35-mm Cu filter or a Gammacell 1000 (Atomic Energy of Canada, Ottawa) with a $^{137}$Cs source emitting at a fixed dose rate of 14.3 Gy/min as determined by dosimetry. Control cells were exposed to the same conditions but not irradiated.

Northern Blot Analysis. Total cellular RNA was isolated as described (29). RNA (20 µg per lane) was separated in an agarose/formaldehyde gel, transferred to a nitrocellulose filter, and hybridized to the following $^{32}$P-labeled DNA probes: (i) the 1.8-kilobase (kb) BamHI/EcoRI c-Jun cDNA (30); (ii) the 0.91-kb Sca I/Nco I c-fos DNA consisting of exons 3 and 4 (31); (iii) the 1.8-kb EcoRI Jun-B cDNA isolated from the p465.20 plasmid (32); and (iv) the 2.0-kb PstI β-actin cDNA purified from pA1 (33). The autoradiograms were scanned using an LKB UltroScan XL laser densitometer and analyzed using the LKB GelScan XL software package. The intensity of c-Jun hybridization was normalized against β-actin expression.

Run-On Transcriptional Analysis. HL-60 cells were treated with ionizing radiation and nuclei were isolated after 3 hours. Newly elongated $^{32}$P-labeled RNA transcripts were hybridized to plasmid DNAs containing various cloned inserts after digestion with restriction endonulceases as follows: (i) the 2.0-kb Pst I fragment of the chicken β-actin pA1 plasmid (positive control); (ii) the 1. 1-kb BamHI insert of the human β-globin gene (negative control); and (iii) the 1.8-kb BamHI/EcoRI fragment of the human c-Jun cDNA from the pBluescript SK(+) plasmid. The digested DNA was run in a 1% agarose gel and transferred to nitrocellulose filters by the method of Southern. Hybridization was performed with $10^7$ cpm of $^{32}$P-labeled RNA per ml of hybridization buffer for 72 h at 42° C. Autoradiography was performed for 3 days and the autoradiograms were scanned as already described.

EXAMPLE 3

Radiation Induced Transcription of Jun and Egr-1

There was increased mRNA expression for different classes of immediate early response to radiation genes (Jun, Egr-1) within 0.5 to 3 hours following cellular x-irradiation. Preincubation with cycloheximide was associated with superinduction of Jun and Egr-1 in x-irradiated cells. Inhibition of protein kinase C (PKC) activity by prolonged stimulation with TPA or the protein kinase inhibitor H7 prior to irradiation attenuated the increase in Egr-1 and Jun transcripts. These data implicated Egr-1 and Jun as signal transducers during the cellular response to radiation injury and suggested that this effect is mediated in part by a protein kinase C (PKC) dependent pathway.

Jun homodimers and Jun/fos heterodimers regulate transcription by binding to AP1 sites in certain promoter regions (Curran and Franza, 1988). The Jun and fos genes are induced following x-ray exposure in human myeloid leukemia cells suggests that nuclear signal transducers participate in the cellular response to ionizing radiation.

The Egr-1 and Jun genes are rapidly and transiently expressed in the absence of de novo protein synthesis after ionizing radiation exposure. Egr-1 and Jun are most likely involved in signal transduction following x-irradiation. Down-regulation of PKC by TPA and H7 is associated with attenuation of Egr-1 and Jun gene induction by ionizing radiation, implicating activation of PKC and subsequent induction of the Egr-1 and Jun genes as signaling events which initiate the mammalian cell phenotypic response to ionizing radiation injury.

Control RNA from unirradiated cells demonstrated low but detectable levels of Egr-1 and Jun transcripts. In contrast, Egr-1 expression increased in a dose dependent manner in irradiated cells. Levels were low but detectable after 3 Gy and increased in a dose dependent manner following 10 and 20 Gy. Twenty Gy was used in experiments examining the time course of gene expression so that transcripts were easily detectable. Cells remained viable as determined by trypan blue dye exclusion during this time course. A time dependent increase in Egr-1 and Jun mRNA levels was observed. SQ-20B cells demonstrated coordinate increases in Egr-1 and Jun expression by 30 minutes after irradiation that declined to baseline within 3 hours. In contrast, Egr-1 transcript levels were increased over basal at 3 hours while Jun was increased at one hour and returned to basal at 3 hours in AG1522. Jun levels were increased at 6 hours in 293 cells while Egr-1 was increased at 3 hours and returned to basal levels by 6 hours.

To determine whether Egr-1 and Jun participated as immediate early genes after x-irradiation, the effects of protein synthesis inhibition by cycloheximide were studied in cell lines 293 and SQ-20B after x-ray exposure. Cycloheximide treatment alone resulted in a low but detectable increase in Egr-1 and Jun transcripts normalized to 7S. In the absence of CHI, the level of Egr-1 and Jun expression returned to baseline. In contrast, SQ-20B cells pretreated with CHI demonstrated persistent elevation of Egr-1 at 3 hours and 293 cells demonstrated persistent elevation of Jun mRNA at 6 hours after irradiation thus indicating superinduction of these transcripts.

mRNA levels of transcription factors Egr-1 and Jun increased following ionizing radiation exposure in a time and dose dependent manner. The potential importance of the induction of Egr-1 and Jun by ionizing radiation is illustrated by the recent finding that x-ray induction of the PDGFα chain stimulates proliferation of vascular endothelial cells (Witte, et al., 1989). PDGF has AP-1 and Egr-1 binding domains while TNF has elements similar to AP-1 and Egr-1 target sequences (Rorsman, et al., 1989; Economou, et al., 1989). X-ray induction of PDGF and TNF are likely regulated by Egr-1 and Jun.

The following is a method used in EXAMPLE 3:

Kinase Inhibitors

Cell line SQ-20B was pretreated with 1 μM TPA for 40 hours to down regulate PKC and then stimulated with TPA, serum, or x-ray (20 Gy). Controls included x-ray without TPA pretreatment, TPA (50 nM) without TPA pretreatment and untreated cells. RNA was isolated after one hour and hybridized to Egr-1. SQ-20B cells were preincubated with 100 μM H7 (1-(5-isoquinolinylsulfonyl)-2-methyl piperazine) or 100 μM HA1004 (N-[2-methylamino] ethyl)-5-isoquino-linesulfonamide) (Seikagaku America, Inc., St. Petersberg, Fla.) for 30 minutes or TPA pretreatment (1 μM) for 40 hours and followed by exposure to 20 Gy x-irradiation. RNA was extracted one hour after irradiation. Positive control cells treated under the same conditions but in the absence of inhibitor also received 20 Gy, while negative control cells received neither H7 nor X-ray. RNA was extracted at one hour after 20 Gy without inhibitor. Northern blots were hybridized to Egr-1 or 7S. 293 cells pretreated with the above inhibitors were irradiated, RNA was extracted after 3 hours and the Northern blot was hybridized to Jun and 7S probes.

EXAMPLE 4

Ionizing Radiation Activates Transcription of the Egr-1 Gene via CArG Domains

The cellular response to ionizing radiation includes cell cycle-specific growth arrest, activation of DNA repair mechanisms and subsequent proliferation of surviving cells. However, the events responsible for the control of this response remain unclear. Recent studies have demonstrated that ionizing radiation exposure is associated with activation of certain immediate-early genes that code for transcription factors. These include members of the Jun/fos and early growth response (Egr) gene families (Sherman, et al., 1990; Hallahan, et al, 1991). Other studies have demonstrated that x-rays induce expression and DNA binding activity of the nuclear factor κB (NF-κB; Brach, et al., 1991).

The activation of these transcription factors may represent transduction of early nuclear signals to longer term changes in gene expression which constitute the response to ionizing radiation. In this context, irradiation of diverse cell types is also associated with increased expression of the TNF, PDGF, FGF and interleukin-1 genes (Hallahan, et al., 1989; Witte, et al, 1989; Woloschak, et al., 1990; Sherman, et al., 1991). Expression of cytokines is conceivably involved in the repair and repopulation associated with x-ray-induced damage to tissues, and may explain some of the organismal effects of ionizing radiation (Hall, 1988). Moreover, it is possible that immediate-early transcription factors serve to induce these changes in gene expression.

The present studies relate to mechanisms responsible for x-ray-induced activation of the Egr-1 gene (also known as zif/268, TIS-8, NFGI-A and Krox-24; Sukhatme, et al., 1988; Christy, et al., 1988; Milbrandt, 1987; Lemaire, et al., 1988; Lim, et al., 1987). The Egr-1 gene encodes a 533-amino acid nuclear phosphoprotein with a $Cys_2$-$His_2$ zinc finger domain that is partially homologous to the corresponding domain in the Wilms tumor-susceptibility gene (Gessler, 1990). The Egr-1 protein binds to the DNA sequence CGCCCCCGC in a zinc-dependent manner and functions as a regulator of gene transcription (Christy, et al, 1989; Cao, et al., 1990; Gupta, et al, 1991). Both mitogenic and differentiation signals have been shown to induce the rapid and transient expression of Egr-1 in a variety of cell types. For example, the Egr-1 gene is induced after mitogenic stimulation of Balb/c-3T3 cells by serum, PDGF or FGF (Lau, et al, 1987; Sukhatme, et al., 1987). The Egr-1 gene is also induced during: 1) cardiac and neuronal differentiation of the pleuripotent EC line (Sukhatme, et al., 1988); and 2) monocytic differentiating of human myeloid leukemia cell lines (Kharbanda, et al., 1991; Bernstein, et al., 1991). While Egr-1 transcription is activated by the protein tyrosine kinase activity of v-src and v-fps (Gius, et al., 1990; Christy, et al., 1989; Homma, et al., 1986), additional work indicates that the serine/threonine kinase activity of c-raf-1 is also involved in mediating inducibility of this gene (Chirgwin, et al., 1979). Other studies have demonstrated that induction of Egr-1 expression is similar to that of c-fos in many situations and that this coordinate regulation is mediated by the presence of serum response elements in both promoters (Sukhatme, et al., 1988; Cleveland, et al., 1980; Wilson, et al., 1978).

Although previous work has demonstrated that ionizing radiation treatment is associated with increases in Egr-1 mRNA levels (Hallahan, et al., 1991), the mechanisms responsible for this effect are unclear. The present studies demonstrate that x-rays activate transcription of the Egr-1 gene. Serum response or CArG domain [$CC(A/T)_6GG$] domains in the 5' promoter of the Egr-1 gene are functional in this response. This is the first report of specific DNA sequences involved in regulating gene transcription by ionizing radiation.

A low but detectable level of 3.4-kb Egr-1 transcripts were present in untreated HL-525 cells. In contrast, treatment with ionizing radiation was associated with an increase in Egr-1 expression that was detectable at 1 hour. Maximal increases (18-fold) in Egr-1 mRNA levels were obtained at 3 hours, while longer intervals were associated with down-regulation to nearly that in control cells. This transient induction of Egr-1 expression occurred in the absence of significant changes in actin mRNA levels.

Nuclear run-on assays were performed to determine whether x-ray-induced increases in Egr-1 transcripts are controlled at the transcriptional level. There was no detectable transcription of the β-globin gene (negative control) in HL-525 cells, while the actin gene (positive control) was transcribed constitutively. Moreover, treatment with ionizing radiation had little effect on transcription of these genes. However, while transcription of the Egr-1 gene was detectable at low levels in control cells, treatment with ionizing radiation resulted in a 30-fold increase in this rate. Taken together, these findings indicated that x-ray-induced Egr-1 expression is controlled substantially by transcriptional mechanisms.

In order to identify cis elements responsible for x-ray-induced Egr-1 transcription, the Egr-1 promoter region extending from position −957 upstream to the transcription start site to position +248 was ligated to the CAT reporter gene (plasmid pEgr-1 P1.2). This region contains several putative cis elements including two AP-1 sites and six CArG domains (Christy, et al., 1989; Gius, et al., 1990). Treatment of the pEgr-1P1.2 transfected cells with ionizing radiation was associated with a 4.1-fold increase in CAT activity as compared to transfected but unirradiated cells. In contrast, similar studies performed with plasmid pΔgr-1 P1.2 (−550 to −50 deleted) demonstrated little if any inducibility by x-rays. These data suggested that x-ray inducibility of Egr-1 is mediated by sequences present between −550 and −50 of the Egr-1 promoter. Indeed, irradiation of pE425 transfected cells was associated with a 3.6-fold induction of CAT activity compared to that in non-irradiated cells transfected with this construct.

A series of deleted Egr-1 promoter constructs was next used to further define the x-ray responsive elements in pE425. These constructs have been previously described and are shown schematically in Scheme 1. Sequential deletion of the three distal CArGs progressively decreased CAT activity. pE395 (first CArG deleted) conferred x-ray inducibility to a lesser extent than pE425. Deletion of the first and second (pE359) CArGs resulted in further decreases in CAT activity, while deletion of the first three CArG domains (pE342) was associated with little if any increases in CAT activity. Taken together, these findings supported the hypothesis that the three distal CArG elements confer x-ray inducibility of the Egr-1 gene.

Other studies were performed with fragments of the Egr-1 promoter linked to HSV-TK and the CAT gene. There was no detectable inducibility of pTK35CAT by x-rays. In contrast, pE425/250TK, which contains the four distal CArG domains, was more responsive to x-ray treatment than pTK35CAT. The region from −395 to −250, which excludes the first CArG element, was also functional in conferring x-ray inducibility to the heterologous promoter, but to a lesser extent than pE425/250TK. While these findings provided further support for the involvement of CArG domains in x-ray induced Egr-1 transcription, other sequences between these domains could be the functional cis elements. X-ray inducibility of pTK35CAT transcription was also demonstrated with the first CArG with seven base pairs of the 5' and 3' flanking sequences (pSRE1TK).

Since the results of the transient expression assays indicated that the CArG domain is the target sequence for x-ray-mediation activation of the Egr-1 gene, other studies were performed to determine whether nuclear proteins interact with this element and whether x-ray treatment alters this interaction. Nuclear extracts from untreated and x-ray-treated cells were incubated with a $^{32}P$-labeled probe encompassing the first CArG domain. Nuclear proteins from control cells resulted in the formation of several DNA-protein complexes. A similar pattern was obtained with nuclear proteins from x-ray-treated cells. In order to determine which complexes reflected CArG-protein binding, increased amounts of unlabeled probe were preincubated with the nuclear proteins. In these experiments, a 100-fold excess of unlabeled probe completely inhibited formation of the complex with least mobility. In contrast, addition of an oligonucleotide containing the unrelated NF-κB consensus sequence had no effect on the intensity of this complex. These findings and the results of similar gel retardation studies with this labeled fragment (Cleveland, et al., 1980) indicate that the upper complex represents specific CArG-protein interaction.

The following methods were used in Example 4.

Cell Cultures. Human HL-525 myeloid leukemia cells (Jamal, et al., 1990) were maintained in RPMI 1640 medium containing 20% fetal bovine serum (FBS) with 1 mM L-glutamine, 100 U/ml penicillin and 100 μg/ml streptomycin. Irradiation (20 Gy) was performed at room temperature using a Gammacell 1000 (Atomic Energy of Canada Ltd., Ontario) with a $^{137}Cs$ source emitting at a fixed dose rate of 13.3 Gy/min as determined by dosimetry.

Isolation and analysis of RNA. Total cellular RNA was purified by the guanidine isothiocyanate-cesium chloride technique (Grosschedl, et al., 1985). The RNA was analyzed by electrophoresis through 1% agarose formaldehyde gels, transferred to nitrocellulose filters, and hybridized to the following $^{32}p$-labeled DNA probes: 1) the 0.7-kb non-zinc finger insert of a murine Egr-1 cDNA (9); and 2) the 2.0-kb PstI insert of a chicken β-actin gene purified from the pA1 plasmid (Dignam, et al., 1983). Hybridizations were performed at 42° C. for 24 h in 50% (v/v) formamide, 2×SSC, 1×Denhardt's solution, 0.1% SDS, and 200 µg/ml salmon sperm DNA. The filters were washed twice in 2×SSC-0.1% SDS at room temperature and then in 0.1×SSC- 0.1% SDS at 60° C. for 1 h. Signal intensity was determined by laser densitometry and normalized to that for the actin control.

Nuclear run-on assays. Nuclei were isolated from 10 cells and suspended in 100 µl glycerol buffer (50 mM Tris-HCl, pH 8.3, 40% glycerol, 5 mM $MgCl_2$, and 0.1 mM EDTA). An equal volume of reaction buffer (10 mM Tris-HCl, pH 8.0, 5 mM $MgCl_2$, 100 mM KCl, 1 mM ATP, 1 mM CTP, 1 mM GTP, and 5 mM dithiothreitol) was added to the nuclei in suspension and incubated at 26° C. for 45 min with 250 µCi [$\alpha$-$^{32}$p] UTP (3000 Ci/mmol; Dupont, Boston, Mass.). The nuclear RNA was isolated as described (Kharbanda, et al., 1991) and hybridized to the following DNAs: 1) a 1.1-kb BamHI insert of a human β-globin gene (negative control) (Hallahan, et al., 1991); 2) a PstI digest of the pA1 plasmid containing a fragment of the chicken β-actin gene (positive control) (Dignam, et al., 1983); and 3) the 0.7-kb insert of the murine Egr-1 cDNA (Sukhatme, et al., 1988). The digested DNAs were run in 1% agarose gels and transferred to nitrocellulose filters. Hybridizations were performed with $10^7$ cpm of $^{32}$P-labeled RNA/ml in 10 mM Tris-HCl, pH 7.5, 4×SSC, 1 mM EDTA, 0.1% SDS, 2×Denhardt's solution, 40% formamide, and 100 µg/ml yeast tRNA for 72 h at 42° C. The filters were washed in: a) 2×SSC-0.1% SDS at 37° C. for 30 min; b) 200 ng/ml RNase A in 2×SSC at room temperature for 5 min; and c) 0.1×SSC-0.1% SDS at 42° C. for 30 min.

Reporter assays. The pEgr-1 P1.2, pE425, pE395, pE359, pE342, pE125, pE98 and pE70 constructs were prepared as described (26). pE425/250TK was constructed by cloning a HindIII-SmaI fragment from pE425, spanning the region −425 to −250 of the Egr-1 promoter, upstream of the herpes simplex virus thymidine kinase (HSV-TK) promoter in plasmid pTK35CAT (Homma, et al., 1986). pE395/250TK was constructed in the same manner using a HindIII-SmaI fragment from pE395. pSRE1TK contains the 5'-most distal or first CArG domain in the Egr-1 promoter along with seven base pairs of the 5' and 3' flanking sequences cloned into the SalI-BamHI site of pTK35CAT (Homma, et al., 1986). The constructs were transfected into cells using the DEAE-dextran technique (Treisman, et al., 1990). Cells ($2 \times 10^7$) were incubated in 1 ml of Tris-buffered saline solution (25 mM Tris-HCl, pH 7.4, 137 mM NaCl, 5 mM KCl, 0.6 mM $Na_2HPO_4$, 0.7 mM $CaCl_2$, and 0.7 mM $MgCl_2$ containing 0.4 mg DEAE-dextran and 8 µg plasmid, at 37° C. for 45 min. The cells were washed with media containing 10% FBS, resuspended in complete media and then incubated at 37° C. Thirty-six h after transfection, one aliquot of the cells served as a control and the other was treated with ionizing radiation. The cells were harvested after 8 hours and lysed by three cycles of freezing and thawing in 0.25M Tris-HCl, pH 7.8, and 1 µM phenylmethylsulfonyl-fluoride. Equal amounts of the cell extracts were incubated with 0.025 µCi [$^{14}$C]chloramphenicol, 0.25M Tris-HCl, pH 7.8 and 0.4 mM acetyl-coenzyme A for 1 hour at 37° C. The enzyme assay was terminated by addition of ethyl acetate. The organic layer containing the acetylated [$^{14}$C] chloramphenicol was separated by thin-layer chromatography using chloroform:methanol (95%:5%; v/v). Following autoradiography, both acetylated and unacetylated forms of [$^{14}$C]chloramphenicol were cut from the plates, and the conversion of chloramphenicol to the acetylated form was calculated by measurement of radioactivity in a β-scintillation counter.

Gel retardation assays. Nuclear extracts were prepared as described (Fisch, et al., 1987). A 40 bp synthetic double-stranded oligonucleotide containing the first CArG element (Cleveland, et al., 1980) was end-labeled with [$\alpha$-$^{32}$p] dCTP using T4 polynucleotide kinase and then purified in a 5% polyacrylamide gel. The purified end-labeled probe (1 ng; approx. $1 \times 10^5$ cpm) was incubated with varying amounts of nuclear protein extract for 15 min at 20° C. in a buffer containing 12 mM HEPES, pH 7.9, 60 mM KCl, 1 mM EDTA, 5 mM dithiothreitol, 6% (v/v) glycerol, 1 µg bovine serum albumin, and 0.25 µg of sonicated salmon sperm DNA. Competition experiments were performed with either unlabeled probe or a 22 bp oligonucleotide containing the NF-κB binding site. Competing oligonucleotides were pre-incubated with the nuclear protein extract for 20 min at 4° C. before adding the labeled probe. The final reaction products were analyzed by electrophoresis in a 5% polyacrylamide gel containing ¼×TBE (22 mM Tris, 22 mM boric acid, 0.5 mM EDTA) and subsequent autoradiography.

In the present studies, HL-525 cells responded to ionizing radiation with induction of Egr-1 mRNA levels. These findings indicated that ionizing radiation increases Egr-1 expression through signaling pathways distinct from those activated during induction of this gene in TPA-treated cells. Furthermore, the finding that x-ray-induced TNF gene expression is attenuated in the HL-525 line (Gilman, 1988) suggests that ionizing radiation induces the Egr-1 and TNF genes by distinct signaling pathways in these cells.

These studies further demonstrate that x-ray-induced Egr-1 expression is regulated at least in part by transcriptional mechanisms. Nuclear run-on assays demonstrated an increase in the rate of Egr-1 gene transcription following ionizing radiation. Moreover, analysis of the full length Egr-1 promoter (pEgr-1P1.2) in transient expression assays demonstrated inducibility by ionizing radiation. Transfection of pΔEgr-1P1.2 (−550 to −50 deleted) and pE425 provided additional evidence that the promoter region containing the six CArG elements was responsible for conferring x-ray inducibility. These findings were supported by the use of several other deleted promoter constructs which indicated that the region encompassing the first three CArG elements is functional in the x-ray response.

In this context, sequential deletion of these distal CArGs progressively eliminated the x-ray response. The four distal CArGs also conferred x-ray inducibility to a heterologous promoter and this effect was decreased by deleting the first CArG domain. More importantly, studies with the first CArG domain demonstrated that this element was sufficient to confer the x-ray response. Taken together, these findings strongly support the CArG domain as the radiation responsive element.

EXAMPLE 5

Radiation Signalling Mediated by Jun Activation

Ionizing radiation produces a wide range of effects on cells which include induction of mutations, lethality, malignant transformation in some surviving cells, cell cycle arrest, and subsequent proliferation of cells. Jun, a transcription factor that is central to tumor promotion, proliferation and cell cycle regulation, is activated by DNA damaging agents in mammalian cells (Devary, 1991 and Bernstein, 1989). One proposed mechanism of Jun activation is through dissociation of Jun from an inhibitor of Jun transcription (Baichwal, 1990).

To investigate protein binding to the AP-1 sequence following irradiation, nuclear proteins were extractd from irradiated human sarcoma cell line RIT-3 cells at 5 minutes intervals for 30 minutes following exposure to 10 Gy. The AP-1, NFκB, SP-1 and CTF binding sequences labeled with $^{32}$P were incubated with cell extracts. DNA-protein mixtures were then separated by electrophoresis. An increase in nuclear protein binding to AP-1 DNA sequences was found at 10 to 20 minutes following irradiation as compared to untreated control cells in electrophoretic mobility shift assay, whereas there was no increase in nuclear protein binding to NF-κB, SP-1, Oct-1 or CTF following irradiation of RIT-3 cells.

DNA-protein complexing was not prevented by adding the inhibitor of protein synthesis cycloheximide, to cells prior to irradiation. AP-1 binding was eliminated when nonlabeled AP-1 consensus sequence (Rauscher, 1988) competed for nuclear protein when added to extracts prior to the addition of labeled AP-1 and eliminated the banding produced by extracts from irradiated RIT-3 cells. In contrast, a nonspecific DNA sequence (Oct-1) did not compete for nuclear protein binding. These data indicated that nuclear protein binding to AP-1 following irradiation is specific.

To determine whether AP-1 binding nuclear proteins from irradiated RIT-3 cells share epitopes with known transcription factors, Jun and fos antisera (Chiles, 1991 and Stopera, 1992) were added to nuclear extracts prior to the addition of labeled AP-1 DNA sequences. The addition of antiserum to the DNA binding domains of fos (Ab-2) and Jun (CRB) resulted in a reduction in protein complexing to the AP-1 sequence following irradiation. Increasing concentrations of antiserum progressively reduced protein-DNA complexes accordingly. These data indicate that proteins that bind the AP-1 sequence following irradiation have epitopes recognized by antiserum to the DNA binding domains of Jun and fos.

To determine whether activated Jun results in increased transcription of the AP-1 binding site following ionizing radiation exposure, the plasmid (p3xTRE-CAT) containing three AP-1 sites upstream of the minimal tk promoter (pBLCAT2) was transfected into RIT-3 cells. Irradiation of p3xTRE-CAT transfectants resulted in a 3 fold increase in CAT expression. To determine whether the c-Jun promoter is induced by radiation in a manner analogous to serum and phorbol esters, the 1840-base pair segment of the c-Jun promoter placed upstream of the chloramphenicol acetyl transferase (CAT) gene [Angel, 1988] was transfected into RIT-3 cells. Following transfection, cells were maintained in 0.2% fetal calf serum (FCS) and irradiated (10 Gy, 2 Gy/min) 40 hrs post-transfection and CAT was extracted 5 hours after irradiation.

Transfection of the −1.1 kb to +740-bp region of the c-Jun promoter (c-Jun-CAT) demonstrated a 3-fold increase in gene expression following exposure to ionizing radiation. Transfection of the plasmid with a deletion of the AP-1 site located at +150-bp (−132/+170 ΔAP-1CAT) resulted in a loss of x-ray-mediated induction. These results suggest that activated AP-1 participates in the transcription of c-Jun and that the AP-1 DNA sequence is sufficient and necessary to confer x-ray-mediated gene induction.

Several regulatory and DNA binding domains exist within the Jun protein. Close to the DNA binding domain is a region designated as $A_2$, which is required to activate transcription (reviewed in (Lewin, 1991). $A_1$, an additional transcriptional activation domain is found near the N terminus adjacent to a region termed Delta (Δ) which is proposed to bind a cellular protein that inhibits the transcriptional activating properties of Jun (Baichwal, 1990 and Baichwal, 1991). Jun transcriptional activity can be conferred through either or both activation domains $A_1$ and $A_2$. Phorbol ester treatment results in the modification of the Jun protein by a protein kinase C (PKC)-dependent phosphorylation of the $A_1$ region and thereby autoinduces transcription of c-Jun (Binetruy, 1991 and (Pulverer, 1991).

Increased Jun binding to AP-1 sequences following irradiation indicate that Jun protein is modified following irradiation. Taken together with the recent findings that PKC is activated following irradiation of cells and that PKC depletion suppress c-Jun induction by irradiation (Hallahan, 1992), the data suggest that X-ray exposure activates Jun through PKC modification of the $A_1$ domain (Binetruy, 1991 and Pulverer, 1991).

Two plasmids were transfected into HeLa and RIT-3 cells to study activation of the transcriptional potential of Jun protein following irradiation. pSG-Jun5-253 contains the SV40 promoter, which is not transcriptionally responsive to radiation, upstream of the coding sequence for Δ, $A_1$, and $A_2$ (Baichwal, 1990). The DNA binding domain of Jun was replaced with the DNA binding domain of the yeast GAL4 gene which encodes a protein involved in yeast transcriptional regulation (Baichwal, 1990). A second plasmid, G5BCAT contains the DNA sequence which binds Gal4 protein placed 5' of the E1b TATA box upstream of the CAT reporter gene (Baichwal, 1990). When the activation domain of Jun protein becomes transcriptionally active, the chimeric Gal-Jun protein, initiates CAT transcription following binding to the Gal4 binding sequence.

These plasmids were co-transfected by calcium phosphate precipitation into HeLa and RIT-3 cells. Transfectants were irradiated with 20 Gy and demonstrated a three-fold increase in CAT activity as compared to untreated controls. This level of expression was comparable to that observed following TPA stimulation which produced a 3.5 fold increase in CAT activity. Irradiation of RIT-3 cells transfected with G5BCAT alone demonstrated no increase in CAT activity. Similar results were obtained in HeLa cells which contain the Jun inhibitor. However, Hep G2 cells which do not contain the Jun inhibitor [Baichwal, 1990] demonstrated no x-ray-induced activation of the Gal4-Jun chimeric. These data suggest that the Gal-Jun chimeric protein is activated following irradiation resulting in DNA binding to accelerate transcription of CAT.

Because x-ray induced c-Jun gene expression is attenuated when PKC is depleted or inhibited, the PKC inhibitor H7 was added to RIT-3 cells transfected with pSG-Jun5-235 and G5BCAT. H7 treatment abrogated the x-ray induced increase in CAT activity. This finding is consistent with previous results that demonstrated X-ray-induced PKC activation is required for gene expression (Hallahan, 1991).

The inhibitor of Jun transcription that binds to the Δ/$A_1$ domains represses the transcriptional activity of $A_1$. The inhibitor of Jun transcription was originally defined in experiments where an excess of Jun competed for inhibitor and thereby allowed uninhibited Jun to increase transcription of the G5-CAT construct when compared to untreated control cells. Based on these results, HeLa cells are reported to contain the Jun inhibitor (Baichwal, 1990) whereas, in HepG2 cells do not. To determine whether the Jun inhibitor is present in RIT-3 cells, the expression vector CMV-Jun, which constitutively expresses c-Jun, was cotransfected with pSGJun5-235 and G5BCAT. Basal expression of CAT increased in RIT-3 and HeLa cells but not HepG2 when CMV-Jun was added. These results confirm and extend the results of Tijan et al. in that Hela and RIT-3 cells contain the Jun inhibitor but not HepG2 cells. Cells that contain the Jun inhibitor demonstrate an increase in radiation mediated transcription of G5BCAT, whereas cells that do not contain the inhibitor of Jun show no increase in transcription of G5BCAT.

RIT-3 cells cotransfected with CMV-Jun, pSGJun5-235 and G5BCAT do not demonstrate an increase in transcription as compared to these transfectants treated with identical conditions, but no irradiation. These data suggest that dissociation from the Jun inhibitor may be one mechanism of regulating radiation-mediated transcription.

The following methods were used in Example 5.

Nuclear Extracts. Nuclear extracts were prepared according to previously described methods (Schreiber, 1989) at 10,20,30, and 60 min. after irradiation. RIT-3 cells ($10^6$) were washed in 10 ml PBS, scraped, and pelleted by centrifugation at 1500 g for 5 min. The pellet was resuspended in 1 ml PBS, transferred into an Eppendorf tube and pelleted again for 15 sec. PBS was removed and the cell pellet resuspended in 400 µl of cold buffer A (10 mM HEPES pH 7.9; 10 mM KCl; 0.1 mM EDTA; 1 mM DTT; 0.5 mM PMSF). The cells were allowed to swell on ice for 15 min, followed by the addition of 25 ml of 10% NP-40. The mixture was centrifuged for 30 sec and the nuclear pellet resuspended in 50 µl ice-cold buffer B (20 mM HEPES pH 7.9; 0.4M NaCl; 1 mM EDTA; 1 mM EGTA; 1 mM DTT; 1 mM PMSF) for 15 min and the nuclear extract centrifuged for 5 min. Protein content was determined by the Bradford method (Bio-Rad). The AP-1 consensous sequence DNA (BRL-GIBCO) was end-labeled with [$-^{32}$P]dATP using DNA polymerase I Klenow fragment.

Binding Assays. Binding assays were performed by incubating the end-labeled DNA (1 ng) with 10 µg nuclear protein, 75 mM KCl and 1 µg/ml poly (dI-dC) in a 20 µl reaction for 20 min at room temperature.

Competition Assays. Competition studies were performed using oligonucleotides corresponding to known cis-acting elements AP-1, and Oct-1 (BRL-GIBCO) at a 100-fold molar excess as compared to the labeled fragments. The reaction products were separated by 5% polyacrylamide gel electrophoresis, dried and analyzed by autoradiography.

Antisera Studies. Antisera to Jun and fos proteins reduced radiation-induced AP-1 binding. A. Antiserum to human transcription factors c-Jun (amino acids 73-87, Ab-2, Oncogene Sci.), c-Jun, Jun-B, Jun-D (Cambridge Research, log OA-11-837), and c-fos (amino acids 4-17, Ab-2, Oncogene Sci and (amino acids 1-14, Lot OA-11-823, Cambridge Research) were added to 10 µg of nuclear extracts at a 1:200 dilution and incubated at 24° C. with rocking for one hour. DNA segments were added as described above followed by separation using electrophoretic mobility shift assays.

Transfection Assays. Plasmids contain c-Jun-CAT, 3xTRE-CAT, and ΔAP-1-CAT (2 µg) were cotransfected with a plasmid containing a CMV promoter linked to the β-galactosidase gene (1 µg) and 12 µg of carrier DNA into RIT-3 cells. Cells were transfected using Lipofectin Reagent (BRL-GIBCO) for 20 hrs., followed by the addition of medium with 0.2% fetal bovine serum. Transfectants were incubated for 40 h after transfection followed by treatment with 10 Gy (1 Gy/min, GE Maxitron) ionizing radiation and harvested by scraping 6 h later. The cells were lysed and extracts were incubated with [$^{14}$C]chloramphenicol and acetyl coenzyme A for one hour at 37° C. CAT activity was determined by separating acetylated-[$^{14}$C]chloramphenicol by ascending chromatography. Scintillation counting of both the nonacetylated and acetylated forms of [$^{14}$C] chloramphenicol was used to quantify CAT activity. shown above are the results of: The 1.1 Kb segment of the c-Jun promoter linked to CAT (c-Jun-CAT). The 3xTRE-CAT. The ΔAP-1-CAT plasmid in which the AP-1 sequence has been deleted from the c-Jun promoter. CAT activity is compared to nonirradiated and TPA treated transfectants. The mean and standard errors of 3 experiments are presented.

Plasmids pSG-Jun5-253 (2 µg) and G5BCAT (4 µg) were cotransfected with a plasmid containing a CMV promoter linked to the β-galatosidase gene (1 µg) and 12 µg of carrier DNA into RIT-3 and HeLa cells using lipofection. CAT activity is compared to nonirradiated and TPA treated transfectants. The mean and standard errors of 3 experiments are presented.

EXAMPLE 6

Involvement of Reactive Intermediates in the Induction of c-Jun Gene Transcription by Ionizing Radiation Ionizing radiation has been postulated to induce activation of DNA repair mechanisms, cell cycle arrest in $G_2$ phase and lethality by either direct interaction with DNA or through the formation or reactive oxygen intermediates (ROI) which damage DNA. Recent studies have further suggested a role for the activation of immediate-early genes in the response to ionizing radiation. For example, exposure of cells to x-rays is associated with activation of the c-Jun/c-fos and Egr-1 gene families which code for transcription factors. Other studies have demonstrated that ionizing radiation induces expression and DNA binding activity of the nuclear factor κB (NF-κB). The activation of transcription factors likely represents a critical control point in transducing early nuclear signals to longer term changes in gene expression that reflect the response to x-ray-induced damage. Studies have demonstrated that radiation treatment is associated with increased expression of certain cytokines, including TNF, platelet-derived growth factor, fibroblast growth factor and interleukin-1. The increase in TNF expression following exposure to ionizing radiation is regulated by transcriptional mechanisms, although it is not known which DNA binding proteins confer this inducibility.

The c-Jun gene codes for the major form of the 40–44 kD AP-1 transcription factor. As observed in irradiated cells, this gene is induced as an immediate early event in response to phorbol esters and certain growth factors. The Jun/AP-1 complex binds to the heptomeric DNA consensus sequence TGA$^G/_C$TCA. The DNA binding domain of c-Jun is shared by a family of transcription factors, including Jun-B, Jun-D and c-fos. Moreover, the affinity of c-Jun binding to DNA is related to the formation of homodimers or heterodimers with products of the fos gene family.

Jun-B also forms dimers and binds to the AP-1 element, although the trans-acting properties of Jun-B differ from those of c-Jun. While the product of the Jun-D gene also interacts with c-fos and has similar binding properties to that of c-Jun, the function of Jun-D is unknown. Certain insights are available regarding the signals which contribute to the regulation of these genes. For example, the finding that phorbol esters activate c-Jun transcription in diverse cell types has implicated the involvement of a phosphorylation-dependent mechanism. A similar pathway appears to play a role, at least in part, in the induction of c-Jun expression by ionizing radiation. In this regard, prolonged treatment with phorbol esters to down-regulate PKC is associated with decreases in the effects of x-rays on c-Jun transcription. Furthermore, non-specific inhibitors of PKC, such as the isoquinolinesulfonamide derivative H7, block x-ray-induced c-Jun expression. Taken together with the demonstration that ionizing radiation induces an activity with characteristics of PKC, these findings have suggested that PKC or a related kinase transduces signals which confer x-ray inducibility of the c-Jun gene.

The present studies examined the effects of ionizing radiation on c-Jun expression in an HL-60 cell variant, designated HL-525, which is deficient in PKC-mediated signal transduction. This variant is resistant to both phorbol ester-induced differentiation and x-ray-induced TNF gene expression. The present results demonstrate that HL-525 cells are also resistant to the induction of c-Jun expression by phorbol esters. The results also demonstrate that treatment of these cells with ionizing radiation is associated with a superinduction of c-Jun mRNA levels compared to phorbol ester-responsive HL-60 cells. The findings indicate that this effect of ionizing radiation is related at least in part to the formation of reactive oxygen intermediates.

Previous studies have demonstrated that treatment of HL-205 cells with TPA is associated with translocation of PKC activity from the cytosolic fraction to the cell membrane, while no cellular redistribution of PKC is detectable during similar exposures of HL-525 cells. Because previous work has suggested that ionizing radiation induces early response gene expression by a PKC-dependent mechanism, studies were performed to determine the effects of x-rays on a cell, such as HL-525, which is deficient in PKC-mediated signal transduction. A low level of c-Jun transcripts was detectable in untreated HL-205 cells, while treatment with ionizing radiation was associated with a transient increase which was maximal at 3 hours. The kinetics and intensity of this response were identical to that reported for the parent HL-60 cells. Expression of the c-Jun gene was also low in untreated HL-525 cells. However, exposure of these cells to ionizing radiation resulted in c-Jun mRNA levels which at 3 h were 3.5-fold higher than that obtained in HL-205 cells. Higher levels of c-Jun expression were similarly detected in HL-525 cells at 6 and 8 h after x-ray exposure. Expression of the Jun-B and Jun-D genes was also transiently increased following x-irradiation of the HL-205 line. Similar findings were obtained with HL-525 cells, although mRNA levels for Jun-B and Jun-D at 3 hours were 2.0- and 2.5-fold higher at 3 hours in this variant as compared to that in HL-205 cells.

Proteins encoded by members of the Jun gene family can form heterodimers with fos gene products. Consequently, the effects of x-rays on c-fos and fos-B expression were also studied. c-fos transcripts were present at low levels in HL-205 cells and there was little if any effect of ionizing radiation on expression of this gene. Similar findings were obtained for fos-β. In contrast, while expression of c-fos and fos-B was also low in HL-525 cells, x-ray exposure was associated with transient increases in transcripts for both of these genes. The kinetics of these increases in fos gene expression were similar to that obtained for members of the Jun gene family. Thus, activation of multiple Jun and fos genes could contribute to diverse nuclear signals in the response of cells to x-rays.

Treatment of HL-60 cells and other myeloid leukemia cells with TPA is associated with induction of the c-Jun gene. Similar effects were obtained in TPA-treated HL-205 cells. The response of these cells to TPA was associated with increases in c-Jun expression that were detectable at 6 hours and reached maximal levels by 24 hours. In contrast, similar exposures of HL-525 cells to TPA resulted in an increase in c-Jun expression which was transient at 12 hours and attenuated compared to that in the HL-205 link. These findings indicated that HL-525 cells are resistant at least in part to the effects of TPA on Jun/AP-1-mediated signaling events. Since TPA activates PKC and translocation of this enzyme is undetectable in HL-525 cells, the expression of PKC in the HL-205 and HL-525 lines was compared. HL-60 cells have been shown to express the (α- and β-PKC isozymes. Indeed, transcripts for PKCα and PKCβ were detectable in HL-205 cells. However, constitutive expression of both genes was decreased by over 75% in HL-525 cells.

These results suggested that the relative resistance of HL-525 cells to TPA-induced c-Jun transcription could be attributable to low levels of PKC expression. Taken together with the finding that c-Jun expression is superinduced by ionizing radiation in HL-525 cells, these results also suggested that x-ray induced c-Jun expression may be mediated by events independent of PKCα and PKCβ.

In order to further define the mechanisms responsible for induction of c-Jun expression in HL-525 cells, nuclear run-on assays were performed to determine the effects of x-rays on rates of c-Jun transcription. Similar studies were conducted in HL-205 cells for comparative purposes. The actin gene (positive control) was constitutively transcribed in HL-205 cells, while there was no detectable transcription of the β-globin gene (negative control). Similar patterns were observed in HL-525 cells. Transcription of the c-Jun gene was detectable at low levels in both cell types. Moreover, x-ray treatment of the HL-205 and HL-525 lines resulted in a 6- and 5-fold stimulation in the rate of c-Jun transcription, respectively. These findings suggested that other mechanisms, perhaps at the posttranscriptional level, were responsible for the higher levels of c-Jun expression following treatment of HL-525 cells.

In order to address this issue, the stability of c-Jun mRNA after treatment with actinomycin D to inhibit further transcription was studied. The half-life of c-Jun transcripts in x-ray-treated HL-205 cells was 31 minutes. In contrast, stability of these transcripts is irradiated HL-525 cells was increased 3-fold with a half-life of 106 minutes. Taken together, these results indicated that transcriptional activation of the c-Jun gene by x-rays is similar in both cell types and that higher levels of c-Jun expression in the HL-525 variant are related to differences in posttranscriptional control.

The finding that ionizing radiation induces c-Jun expression in the HL-525 cells which exhibit an alternated response of these gene to TPA suggested that PKC-independent pathways may mediate this effect of x-rays. In this context, ionizing radiation is known to induce the formation of ROIs. Moveover, recent studies have demonstrated that $H_2O_2$, another agent that acts through production of ROIs, activates the c-Jun gene in HeLa cells. The effects of ROIs in cells is counteracted by the well characterized antioxidant N-acetyl-L-cysteine (NAC). The exposure of HL-205 cells to 30 mM NAC had little if any effect on constitutive levels of c-Jun transcripts. However, this agent inhibited x-ray-induced increases in c-Jun expression by over 90%. Similar findings were obtained in the HL-525 cells. These inhibitory effects of NAC on x-ray-induced c-Jun expression were mediated by a block in transcriptional activation of the c-Jun gene. While ionizing radiation alone increased the rate of c-Jun transcription in HL-525 cells by 4-fold, the addition of NAC inhibited this response by nearly 90%.

In contrast, NAC had no detectable effect on induction of the c-Jun gene in HL-525 cells by 1-β-D-arabinofuranosylcytosine (ara-C; data not shown), another DNA-damaging agent which incorporates into the DNA strand. The findings indicated that NAC is a specific inhibitor of x-ray-induced c-Jun transcription, presumably through its effects of ROIs.

Previous studies have demonstrated that the cellular response to other diverse classes of DNA-damaging agents, including ara-C, UV light, alkylating agents and etoposide, includes the induction of c-Jun expression. These findings have suggested that DNA damage per se is the signal responsible for activation of this gene. This response also appears to involve a protein kinase down-regulated by prolonged exposure to TPA. Since ROIs damage DNA, studies were performed to determine whether the response to these intermediates also includes a TPA-sensitive mechanism. Treatment of the HL-525 cells with TPA alone for 36–39 hours had no detectable effect on c-Jun mRNA levels. However, pretreatment with this agent blocked the x-ray induced increases in c-Jun expression by over 75%.

Similar studies were performed with bryostatin, an agent distinct from TPA which also transiently activates PKC. Treatment of HL-525 cells with bryostatin for 36 hours had little if any effect on the induction of c-Jun transcripts by ionizing radiation. Since $H_2O_2$ also acts as a DNA-damaging agent through the production of ROIs, similar experiments were performed in HL-525 cells treated with this agent. $H_2O_2$ transiently induced c-Jun expression in these cells and this effect was inhibited by NAC.

Pretreatment with TPA blocked $H_2O_2$-induced increases in c-Jun expression by 80%, while a similar exposure to bryostatin had no detectable effect. Taken together, these findings indicated that agents, such as ionizing radiation and $H_2O_2$ which produced ROIs, induce c-Jun expression by a mechanism down-regulated by TPA and not bryostatin.

NAC counteracts the effects of oxidative stress by scavenging ROIs and increasing intracellular glutathione (GSH). Previous studies have demonstrated that NAC is a potent inhibitor of phorbol ester-induced activation of the HIV-1 long terminal repeat. This antioxidant has also been found to inhibit activation of the nuclear factor κB (NF-κB) by phorbol esters and other agents such as $H_2O_2$. The available findings suggest the release activate NF-κB by induced the release of the inhibitory subunit IκB. ROIs are also formed during the treatment of cells with ionizing radiation. Thus, the cellular response to this agent may involve the ROI-induced activation of transcription factors and thereby longer term effects on gene expression. Indeed, recent work has demonstrated that DNA binding activity and expression of NF-κB is induced following exposure to ionizing radiation. However, ROIs have extremely short half-lives and while DNA-binding of NF-κB is rapidly increased in x-ray-treated cells, it is not clear whether this effect is directly or indirectly related to the formation of oxygen radicals.

The results of the present studies suggest that ROIs also contribute to the activation of c-Jun transcription by ionizing radiation. This event was inhibited by NAC. Moreover, $H_2O_2$ increased c-Jun expression and this effect was similarly inhibited by NAC. While these findings might reflect a nonspecific inhibition of c-Jun expression, NAC had no detectable effect on ara-C-induced increases in c-Jun transcripts. Ara-C damages DNA by incorporation into elongating strands and is not known to mediate its cytotoxic effects through ROIs. Of interest, the cellular response to ara-C also includes activation of NF-κB. Since ROIs damage DNA in irradiated and $H_2O_2$-treated cells, this damage may represent the event in common with agents such as ara-C.

Other studies have suggested that the induction of c-Jun expression by ionizing radiation is mediated by a PKC-dependent mechanism. Prolonged treatment with TPA to down-regulate PKC results in marked attenuation of c-Jun gene by x-rays is also inhibited by H7, a nonspecific inhibitor of PKC, but not by HA1004, a more selective inhibitor of cyclic nucleotide-dependent protein kinases. Consequently, cell lines such as HL-525, which are deficient in PKC-mediated signaling, would likely respond to ionizing radiation with an attenuated induction of c-Jun expression. Indeed, the activation of TNF expression in x-ray-treated HL-525 cells is diminished compared to TPA-responsive HL-60 lines. Furthermore, the present finding that treatment of HL-525 cells with TPA is associated with an attenuated c-Jun response supports a defect in PKC-mediated events that control c-Jun expression. Nonetheless, HL-525 cells responded to ionizing radiation with an increase in c-Jun expression which was in fact more pronounced than that obtained in HL-205 cells.

The results demonstrate that this increase in c-Jun mRNA levels is regulated by activation of c-Jun transcription, as well as a prolongation in the half-life of these transcripts. Other members of the Jun/fos family (Jun-B, Jun-D, c-fos, fos-B) were also induced following x-ray exposure of the HL-525 variant, while treatment of these cells with TPA resulted in little if any effect on expression of these genes. These findings indicated that ionizing radiation increases Jun/fos expression through signaling pathways distinct from those activated during induction of these genes in TPA-treated cells.

The basis for the lack of PKC redistribution in TPA-treated HL-525 cells is unclear. Nonetheless, translocation of PKC from the cytosol to the cell membrane may be necessary for certain TPA-induced signaling events, such as induction of c-Jun expression. However, it is not known whether translocation to the cell membrane is necessary for activation of each of the different PKC isoforms. The present results demonstrate that prolonged treatment of the HL-525 variant with TPA blocks x-ray-induced increases in c-Jun expression. This finding lends support to the involvement of a PKC-dependent mechanism.

The HL-525 variant expresses relatively low levels of PKCα and PKCβ compared to HL-205 cells. Low to undetectable levels of PKC-γ mRNA were also found in both the HL-205 and HL-525 lines (data not shown). Thus, other PKC isozymes which are sensitive to PKC down-regulation may be responsible for transducing signals which confer x-ray inducibility of the c-Jun gene. Alternatively, prolonged TPA treatment could cause down-regulation of other PKC-independent signaling pathways involved in induction of c-Jun by ionizing radiation. X-ray treatment was previously shown to be associated with activation of a PKC-like activity.

The following methods were used in Example 6.

Cell culture. Clone HL-205 was isolated from the human HL-60 myeloid leukemia cell line. The phorbol ester-resistant variant of HL-60 cells, designated HL-525, was isolated by exposing wild-type cells to low concentrations of 12-0-tetradecanoylphorbol-13-acetate (TPA; 0.5 to 3 nM) for 102 passages. These cells were maintained in RPMI 1640 medium containing 20% fetal bovine serum (FBS) with 1 mM L-glutamine, 100 U/ml penicillin and 100 μg/ml streptomycin. Irradiation was performed at room temperature using a Gamma cell 1000 (Atomic Energy at Canada Ltd., Ontario) with a $^{137}$Cs source emitting at a fixed dose rate of 14.3 Gray (Gy)/min as determined by dosimetry.

Isolation and analysis of RNA. Total cellular RNA was purified by the guanidine isothiocyanate-cesium chloride technique. The RNA was analyzed by electrophoresis through 1% agarose-formaldehyde gels, transferred to nitrocellulose filters, and hybridized to the following 32P-labeled DNA probes: 1) the 1.8-kb BamHI/EcoRI insert of a human c-Jun gene purified from a pBluescript SK(+) plasmid; 2) the 1.5-kb EcoRI fragment of the murine Jun-B cDNA from the p465.20 plasmid; 3) Jun-D; 4) the 0.9-kb ScaI/NcoI insert of human c-fos gene purified from the pc-fos-1 plasmid; 5) the 2.0-kb PstI insert of a chicken β-actin gene purified from the pA1 plasmid; and 6) the 1.9-kb BamHI/PstI insert of a human TNF cDNA purified from the pE4 plasmid. Hybridizations were performed at 42° C. for 24 h in 50% (v/v) formamide, 2×SSC, 1×Denhardt's solution, 0.1% SDS, and 200 μg/ml salmon sperm DNA. The filters were washed twice in 2×SSC-0.1% SDS at room temperature and then in 0.1×SSC-0.1% SDS at 60° C. for 1 hour.

Nuclear run-on assays. Nuclei were isolated from $10^8$ cells and suspended in 100 μl glycerol buffer (50 mM Tris-HCl, pH 8.3, 40% glycerol, 5 mM $MgCl_2$, and 0.1 mM EDTA). An equal volume of reaction buffer (10 mM Tris-HCl, ph 8.0, 5 mM $MgCl_2$, 100 mM KCl, 1 mM ATP, 1 mM CTP, 1 mM GTP, and 5 mM dithiothreitol) was added to the nuclei in suspension and incubated at 26° C. for 30 min with 250 μCi [α-$^{32}$P]UTP (3000 Ci/mmol; Dupont, Boston, Mass.). The nuclear RNA was isolated as described and hybridized to the following DNAs: 1) a PstI digest of the pA1 plasmid containing a fragment of the chicken β-action gene; and 2) a BamHI/EcoRI digest of the pBluescript SK(+) plasmid containing a fragment of the human c-Jun gene. The digested DNAs were run in 1% agarose gels and transferred to nitrocellulose filters. Hybridizations were performed with $10^7$ cpm of $^{32}$P-labeled RNA/ml in 10 mM Tris-HCl, ph 7.5, 4×SSC, 1 mM EDTA, 0.1% SDS, 2×Denhardt's solution, 40% formamide, and 100 μg/ml yeast tRNA for 72 h at 42° C. The filters were washed in: a) 2×SSC-0.1% SDS at 37° C. for 30 min; b) 200 ng/ml RNase A in 2×SSC at room temperature for 5 min; and c) 0.1× SSC-0.1% SDS at 42° C. for 30 min.

EXAMPLE 7

Protocol for Treatment of Head and Neck Cancer with X-ray Induced TNF and Therapeutic X-rays For treatment of patients with head and neck cancer, the following steps are followed:

1. Prepare a DNA molecule (genetic construct) comprising a radiation responsive enhancer-promoter operatively linked to an encoding region that encodes a polypeptide.

This construct preferably comprises a CArG domain of an Egr-1 promoter and the gene for the tumor necrosis factor. This construct is designated "construct A" for purposes of this example.

2. "Construct A" is put into a retrovirus that is self-inactivating.
3. Lymphokine activated killer (LAK) cells are infected with the retrovirus bearing "construct A." The cells are to be directed against the malignant cells in the head and neck.
4. The infected LAK cells are infused into the patient to be treated.
5. The head and neck region is irradiated.

The foregoing examples illustrate particular embodiments of the present invention. One of ordinary skill in the art will readily appreciate that changes, modifications and alterations to those embodiments can be made without departing from the true scope spirit of the invention.

REFERENCES

The references listed below and all references cited herein are incorporated herein by reference to the extent that they supplement, explain, provide a background for, or teach methodology, techniques, and/or compositions employed herein.

Alexandropoulos, K., Qureshi, S. A., Rim, M., Sukhatme, V. P., and Foster, D. A. (1992) Nucl. Acids. Res. 20, 2355–2359

Andrews, G. K., Harding, M. A., Calvert, J. P. and Adamson, E. D. (1987) Mol. Cell. Biol. 7, 3452–3458.

Angel, P., Poting, A., Mallick, U., Rahmsdorf, H. J., Schorpp, M., and Herrlich, P. (1986) Mol. Cell. Biol. 6, 1760–1766.

Angel, P., Baumann, I., Stein, B., Dallus, H., Rahmsdorf, H. J., and Herrlich, P. (1987) Mol. Cell. Biol. 7, 2256–2266.

Angel, P. Allegretto, E. A., Okino, S., Hattori, K., Boyle, W. J., Hunter, T. and Karin, M. (1988a) Nature (London) 332, 166–171.

Angel, P., Hattori, K., Smeal, T. & Karin, M. (1988a) Cell 55, 875–885

Attar, R. M., and Gilman, M. Z. (1992) Mol. Cell. Biol. 12, 2432–2443

Baichwal, V. R. & Tjian, R. (1990) Cell 63, 815–825

Baichwal, V. R. & Tjian, R. (1991) Nature 352, 165–168

Ballard (1992) Proc. Natl. Acad. Sci. 89, 1875

Becker, R. C., Corrae, J. M., Harrington, R., et al. (1991) Am. Heart J.

Bernstein, L. R. & Colburn, N. H. (1989) Science 244, 566–569

Bernstein, S. H., Kharbanda, S. M., Sherman, M. L., Sukhatme, V. P., and Kufe, D. W. (1991) Cell Growth and Diff. 2, 273–278

References (cont'd)

Bevelacqua, M. P., Stengelin, S., Gimbrone, M. A., and Seed, B. (1989) Science 243, 1160–1165.

Binetruy, B., Smeal, T. & Karin, M. (1991) Nature 351, 122–127

Bohmann, D., Bos, T. J., Admon, A., Nishimura, T., Vogt, P. K, and Tjian, R. (1987) Science 238, 1386–1392.

Bonura, T. and Smith, K. C. (1976) Int. J. Radiat. Biol 29, 293–296.

Boothman, D. A., Bouvard, I and Hughes, E. N. (1989) Cancer Res. 49, 2871–2878.

Borek, C. (1985) Pharmacol. Ther. 27, 99–142.

Brach, M. A., Hass, R., Sherman, M., Gunji, H., Weichselbaum, R., and Kufe, D. (1991) J. Clin Invest. 88, 691–695

Brenner, D. A., O'Hara, M., Angel, P., Chojikler, M. & Karin, M. (1989) Nature 337, 661–663

Brott, T., Cerebrovase Brain Metab. Rev. 3, 91–113 (1991)

Buscher, M., Rhamsdorf, H. J., Litfin, M., Karin, M., and Herrlich, P. (1988) Oncogene 3, 301–311

Cao, X., Koski, R. A., Gashler, A., McKiernan, M., Morris, C. F., Gaffney, R., Hay, R. V., and Sukhatme, V. P. (1990) Mol. Cell. Biol. 10, 1931–1939

Carswell, E. A. (1975) Proc. Natl. Acad. Sci. USA 72, 3666–3670.

Cathala, G., Savouret, J. F., Mendez, B., West, B. L., Karin, M., Martial, J. A. and Baxter, J. D. (1983) DNA 2, 329–335.

Chaudhary, V. K., FitzGerald, D. J., Adhya, S., et al. (1987) *Proc. Natl. Acad. Sci. USA* 84, 4538–42

Chiles, T., Liu, J. & Rothstein, T. (1991) *J. Immunol.* 146, 1730–1735

References (cont'd)

Chirgwin, J. M., Przybyla, A. E., MacDonald, R. J., and Rutter, W. J. (1979) *Biochemistry* 18, 5294–5299

Christy, B. A., Lau, L. F., Nathans, D. (1988) *Proc. Natl. Acad. Sci. USA* 85, 7857–7861.

Christy, B. A. and Nathans, D. (1989) *Proc. Natl. Acad. Sci.* 86, 8737–8741.

Cleveland, D. W., Lopata, M. A., MacDonald, R. J., Cowan, N. J., Rutter, W. J. and Kirschner, M. W. (1980) *Cell* 20, 95–105.

Curran, T., Franza, B. R. (1988) *Cell* 55, 395–397.

Dalton, S., and Treisman, R. (1992) *Cell* 68, 597–612

Devary, Y., Gottlieb, R. A., et al. (1991) *Mol. Cell. Biol.* 11, 2804–2811

Dewey, W. C. (1979) *Int. J. Radiat. Oncol. Biol. Phys.* 5, 1165–1174.

Dignam, J. D., Lebovitz, R. M., and Roeder, R. G. (1983) *Nucl. Acids. Res.* 11, 1475–1489

Diller (1990) *Molec. Cell Biol.* 10, 5772

Economou, J. S., Rhoades, K., Essner, R., McBride, W. H., Gasson, J. C. and Morton, D. L. (1989) *J. Exp. Med.* 170, 321–326.

Endo, Y. & Tsurngi, K. (1987) *J. Biol. Chem.* 262, 8128–8130

Ezzeddine, Z. D., Martuza, R. L., Platika, D., et al. (1991) *New Biol.* 3, 608–14

Fauser, A. A. (1991) *J. Cell. Biochem.* 45, 353–358

Fisch, T. M., Prywes, R., and Roder, R. G. (1987) *Mol. Cell. Biol.* 8, 2159–2165

Fornace, A. J., Alamo, I., and Hollander, M. C. (1988a) *Proc. Natl. Acad. Sci. USA* 85, 8800–8804.

References (cont'd)

Fornace, A. J., Jr., Schalch, H. and Alamo, I., Jr. (1988b) *Mol. Cell. Biol.* 8, 4716–4720.

Fornace, A. J., Zmudzka, B., Hollander, M. C. and Wilson, S. H. (1989) *Mol. Cell Biol.* 9, 851–853.

Gessler, M. (1990) *Nature* 343, 774–778

Gilman, M. Z. (1988) *Genes Dev.* 2, 394–402

Gius, D., Cao, X., Rauscher, F. J. III, Cohen, D. R., Curran, T., and Sukhatme, V. P. (1990) *Mol. Cell Biol.* 10, 4243–4255

Golumbek, P. T., Lazenby, A. J., Levitsky, H. I., et al. (1991)

Graham, R., and Gilman, M. (1991) *Science* 251, 189–192

Grosschedl, R., and Baltimore, D. (1985) *Cell* 41, 885–897

Gupta, M. P., Gupta, M., Zak, R., and Sukhatme, V. P. (1991) *J. Biol. Chem.* 266, 12813–12816

Hadley, S. W., Wilbur, D. S., Gray, M. A., et al. (1991) *Bioconjug. Chem.* 2, 171–179

Halazonetis, T. D., Georgopoulos, K., Greenberg, M. E., & Leder, P. (1988) *Cell* 55, 917–924

Hall, E. J. (1988) in *Radiobiology for the Radiologist*, ed. Hall, E.J. (Lippincott, Philadelphia), pp. 17–38.

Hallahan, D. E., Spriggs, D. R., Beckett, M. A., Kufe, D. W., and Weichselbaum, R. R. (1989) *Proc. Natl. Acad. Sci. USA* 86, 10104–10107.

Hallahan, D. E., Beckett, M. A., Kufe, D., et al. (1990) *Int. J. Rad. Onc. Biol.* 19, 69–74

References (cont'd)

Hallahan, D. E., Sukhatme, V. P., Sherman, M. L., Virudachalam, S., Kufe, D. W., and Weichselbaum, R. R. (1991a) *Proc. Natl. Acad. Sci. USA* 88, 2156–2160

Hallahan, D. E., Virudachalam, S., Sherman, M. L., Huberman, E., Kufe, D. W., & Weichselbaum, R. R. (1991b) *Cancer Res.* 51, 4565–4569

Hattori, K., Angle, P., LeBeau, M. M., and Karin, M. (1988) *Proc. Natl. Acad. Sci. USA* 85, 9148–9152.

Herrlich, P. (1987) *Accomplishments in Cancer Research* (Lippincott, Philadelphia), pp. 213–228.

Hollander, C. M. and Fornace, A. J., Jr. (1989) *Cancer Res.* 49, 1687–1693.

Homma, Y., Henning-Chub, C. B., and Huberman, E. (1986) *Proc. Natl. Acad. Sci. USA* 83, 7316–7321

Johnson, P., Gray, D., Mowat, M., et al. (1991) *Mol. Cell Biol.* 11, 1–11

Kalderon, D., Roberts, B., Richardson, W. G. and Smith, A. E. (1984) *Cell* 39, 499–509

Kharbanda, S., Nakamura, T., Stone, R., Hass, R., Bernstein, S., Datta, R., Sukhatme, V. P., and Kufe, D. (1991) *J. Clin. Invest.* 88, 571–577

Kolch (1991) *Nature* 349, 426

Lambert, M. and Borek, C. (1988) *J. Natl. Cancer Inst.* 80, 1492–1497

Lau, L. F., and Nathans, D. (1987) *Proc. Natl. Acad. Sci. USA* 84, 1182–1186

Lemaire, P., Revelant, O., Bravo, R., and Charnay, P. (1988) *Proc. Natl. Acad. Sci. USA* 85, 4691–4695

Levine, S. R., & Brott, T. G. (1992) *Prog. Cardiovasc. Dis.* 34, 235–262

Lewin, B. (1991) *Cell* 64, 303–312

Little, J. W. and Mount, D. W. (1982) *Cell* 29, 11–22.

References (cont'd)

Lim, R. W., Varnum, B. C., Herschman, H. R. (1987) *Oncogene* 1, 263–270.

Lory (1988) *J. Bacteriology* 170, 714

Marmorstein, R., Carey, M., Ptashne, M., and Harrison, S. C. (1992) *Nature,* 356, 408–453

Matthews, N., Neale, M. L., Fiera, R. A., Jackson, S. K., and Stark, S. M. (1988) *Tumor Necrosis Factor/Cachectin and Related Cytokinesis*, eds. Bonavida, B., Gifford, G. E., Kirchner, H. & Old, L. J. (Karger, New York), pp. 20–25.

Matthews, N., Neale, M. L., Jackson, S. K. and Stark, J. M. (1987) *Immunology* 62, 153–155.

Milbrandt, J., (1987) *Science* 238, 797–799.

Miskin, R. and Ben-Ishai, R. (1981) *Proc. Natl. Acad. Sci. USA* 78, 6236–6240.

Mitchell, P. J., & Tijan, R. (1989) *Science* 245, 371–378

Moulder, J. E. and Rockwell, S. (1984) *Int. J. Radiat. Oncol. Biol. Phys.* 10, 695–712.

Nakabeppu, Y., Ryder, K., & Nathans, D. (1988) *Cell* 55, 907–915

Neale, M. L., Fiera, R. A. and Matthews, N. (1988) *Immunology* 64, 81–85.

Neta, R., Vogel, S. N., Sipe, J. D., et al. (1988) *Lymphokine Res.* 7, 403–411

Neta, R., Oppenheim, J. J., Schreiber, R. D., et al. (1991) *J. Exp. Med.* 173, 1177–1182

Neta, R., Perlstein, R., Vogel, S. N., et al. (1992) *J. Exp. Med.* 175 689–694

Old, L.J. (1985) *Science* 230, 630–634.

Overell, R. W., Weisser, K.E., Hess, B. W., et al. (1991) *J. Immunol. Methods* 141, 53–62

References (cont'd)

Papathanasiou, M., Barrett, S. F., Hollander, M. C., Alamo, J., Jr., Robbins, J. H., Fornace, A. J., Jr. (1990) *Proc. Ann. Meet. Am. Assoc. Cancer Res.* 31, A1802.

Prywes, R., and Roeder, R. G. (1986) *Cell* 47, 777–784

Prywes, R., Dutta, A., Cromlish, J. A., and Roeder, R. G. (1988) *Proc. Natl. Acad. Sci. USA* 85, 7206–7210

Pulverer, B. J., Kyriakis, J., Avruch, J., et al. (1991) *Nature* 353, 670–674

Qureshi, S. A., Cao, X., Sukhatme, V. P., and Foster, D. A. (1991a). *J. Biol. Chem.* 266, 10802–10806

Qureshi, S. A., Joseph, C. K., Rim, M., Maroney, A., and Foster, D. A. (1991b) *Oncogene* 6, 995–999

Qureshi, S. A., Rim, M., Bruder, J., Kolch, W., Rapp, U., Sukhatme, V. P., and Foster, D. A. (1991) *J. Biol. Chem.* 266, 20594–20597

Rauscher, F. J. (1988) *Cell* 52, 471–480

Roeske, J. C., Chen, G. T., Atcher, R. W., et al. (1990) *Int. J. Radiat. Oncol. Biol. Phys.* 19, 1539–1548

Rollins, B. J. (1992) *Am. J. Respir. Cell Mol. Biol.* 7, 126–127

Rorsman, F., Bywater, M., Knott, T. J., Scott, J. and Betsholtz, C. (1989) *Mol. Cell. Biol.* 8, 571–577.

Rubin, B. Y., Smith, L. J., Hellerman, G. R., Lunn, R. M., Richardson, N. K, and Anderson, S. L. (1988) *Cancer Res.* 48, 6006–6010.

Ryan, Jr., W. A., Franza, Jr., R. B., and Gilman, M. Z. (1989) *EMBO J.* 8, 1785–1792

Ryder, K., Lau, L. F., and Nathans, D. (1988) *Proc. Natl. Acad. Sci. USA* 85, 1487–1491.

References (cont'd)

Sakihama, K., Eizuru, Y. & Minamishima, Y. (1991) *Acta Virol. (Praha)* 35, 127–34

Sariban, E., Imamura, K., Luebbers, R. and Kufe, D. (1988) *J. Clin. Invest.* 81, 1506–1510.

Scanlon, M., Laster, S. M., Wood, J. G. & Gooding, L. R. (1989) *Cell Biol.* 86, 182–186.

Schorpp, M., Mallick, V., Rahmsdorf, H. J. and Herrlich, P. (1984) *Cell* 37, 861–868.

Sersa, G., Willingham, V. and Milas, L. (1988) *Int. J. Cancer* 42, 129–134.

Shaw, P. E., Schroter, H., and Nordheim, A. (1989) *Cell* 56, 563–572

Sheng, M., Dougan, S. T., McFadden, C., and Greenberg, M. E. (1988) *Mol. Cell. Biol.* 8, 2787–2796

Sherman, M. L., Datta, R., Hallahan, D. E., Weichselbaum, R. R., Kufe, D. W. (1990) *Proc. Natl. Acad. Sci. USA* 87, 5663–5666.

Sherman, M. L., Datta, R., Hallahan, D. E., Weichselbaum, R. R., and Kufe, D. W. (1991) *J. Clin, Invest.* 87, 1794–1797

Sherman, M. L., Stone, R. M., Datta, R., Bernstein, S. H. and Kufe, D. W. (1990) *J. Biol. Chem.* 265, 3320–3323.

Steiner, B. (Williams Wilky, 1984) *Treatment of arteriovenous malformations by radiosurgery* 1–295–313

Stopera, S., Davie, J. & Bird, R. (1992) *Carcinogen.* 13, 573–578

Stumpo, D., Stewart, T. N., Gilman, M. Z., and Blackshear, P. J. (1988) *J. Biol. Chem.* 263, 1611–1616

Sugarman, B. J., Aggarwai, B. B., Huas, P. E., Figari, I. S., Palladino, M. A., Jr. and Shepard, H. M. (1985) *Science* 230, 943–945.

References (cont'd)

Sukhatme, V. P., Cao, X., Chang, L. L., Tsai-Morris, C.-H., Stamenkovich, D., Ferreira, P. C. P., Cohen, D. R., Edwards, S. A., Shows, T. B., Curran, T. LeBeau, M. M., and Adamson, E. D. (1988) *Cell* 53, 37–43

Sukhatme, V. P., Kartha, S., Toback, F. G., Taub, R., Hoover, R. G., and Tsai-Morris, C.-H. (1987) *Oncogene* 1, 343–355

Tiefenbrunn, A. J. (1992) *Am. J. Cardiol.* 69

Treisman, R. H. (1986) *Cell* 46, 567–574

Treisman, R. (1990) *Semin. Cancer Biol.* 1, 47–58

Triezanberg, S., Kingsbury, R. C., and McKnight, S. L. (1988) *Genes & Development,* 2, 718–729

Trubetskoy, V. S., Torchilin, V. P., Kennel, S. J., Huang, L. (1992) *Bioconjugate Chem.,* 3, 323–327

Tsai-Morris, C.-H., Cao, X., and Sukhatme, V. P. (1988) *Nucleic Acids Research* 16, 8835–8846

Uckun, F. M., Gillis, S., Souza, L., et al. (1989) *Int. J. Radiol. Onc. Biol. Phys.* 16, 415–435

Unlap, T., Franklin, C. C., Wagner, F., et al. (1992) *Nucleic Acids Res.* 20, 897–902 van Straaten, F., Muller, R., Curran, T., van Beveren, C. and Verma, I. M. (1983) *Proc. Natl. Acad. Sci. USA* 80, 3183–3187.

Waddick, K. G., Song., C. W., Souza L., et al. (1991) *Blood* 77, 2364–2371

Walsh, K. (1989) *Mol. Cell. Biol.* 9, 2191–2201

Wang, A. M., Creasg, A. A., Lander, M. B., Lin, L. S., Strickler, J., Van Arsdell, J. N., Yanamotot, R. and Mark, D. F. (1985) *Science* 228, 149–154.

Weichselbaum, R. R., Nove, J. and Little, J. B. (1980) *Cancer Res.* 40, 920–925.

References (cont'd)

Weichselbaum, R. R., Dahlberg, W., Beckett, M. A., Karrison, T., Miller, D., Clark, J. and Ervin, T. J. (1986) *Proc. Natl. Acad. Sci. USA* 83, 2684–2688.

Weichselbaum, R. R., Beckett, M. A., Simon, M. A., McCowley, C., Haraf, D., Awan, A., Samuels, B., Nachman, J. and Drtischilo, A. (1988) *Int. J. Rad. Oncol. Biol. Phys.* 15, 937–942.

Wilson, J. T., Wilson, L. B., deRiel, J. K., Villa-Komaroff, L., Efstratiadis, A., Forget, B. G. and Weissman, S. M. (1978) *Nucleic Acids Res.* 5, 563–580.

Witte, L., Fuks, Z., Haimovitz-Friedman, A., Vlodavsky, I., Goodman, D. S. and Eldor, A. (1989) *Cancer Res.* 49, 5066–5072.

Woloschak, G. E., Chang-Liu, C. M., Jones, P. S. and Jones, C. A. (1990) *Cancer Res.* 50, 339–344.

Wong (1985) *Science* 228, 149

Wong, G. W. H. and Goeddel, D. V. (1988) *Science* 242, 941–943.

Wong, G. H. W., Elwell, J. H., Oberly, L. H., Goeddel, D. V. (1989) *Cell* 58, 923–931.

Wong, G., McHugh T., Weber, R., et al. (1991) *Proc. Natl Acad. Sci.* 88, 4372–4376

Yamuchi, N., Karizana, H., Watanabe, H., Neda, H., Maeda, M. and Nutsu, Y. (1989) *Cancer Res.* 49, 1671–1675.

Zimmerman, R. J., Chan, A. and Leadon, S. A. (1989) *Cancer Res.* 49, 1644–1648.

Zorial, M., Toschi, L., Ryseck, R. P., Schuermann, M., Muller, R., & Bravo, R. (1989) *EMBO J.* 8, 805–813

Zucker, M. B. & Katz, J. R. (1991) *Proc. Soc. Exp. Biol. Med.* 198, 693–702

What is claimed is:

1. A process of inhibiting growth of a tumor comprising the steps of:
    (a) delivering to said tumor a therapeutically effective amount of a DNA molecule comprising a radiation responsive enhancer-promoter operatively linked to an encoding region that encodes a polypeptide having the ability to inhibit growth of a tumor cell, which encoding region is operatively linked to a transcription-terminating region; and
    (b) exposing said cell to an effective expression-inducing dose of ionizing radiations;
    whereby the polypeptide is expressed and inhibits the growth of said tumor.

2. A process of inhibiting growth of a tumor comprising the steps of:
    (a) delivering to a cell of said tumor a therapeutically effective amount of
        (1) a first DNA molecule comprising a radiation responsive enhancer-promoter operatively linked to an encoding region that comprises:

(i) a first encoding sequence that encodes a DNA binding domain of a first transcription factor;

(ii) a second encoding sequence that encodes an activation or repression domain of a second transcription factor;

(iii) a third encoding sequence that encodes a nuclear localization signal, whereby the first, second and third encoding sequences are operatively linked in frame to each other in any order with the proviso that said third encoding sequence need be present only if said first or second encoding sequence does not encode a nuclear localization signal, and (iv) a transcription-terminating region that is operatively linked to any of the first, second or third encoding sequences such that the transcription-terminating region is located 3' to all of the first, second and third encoding sequences; and (2) a second DNA molecule comprising a binding region that is capable of binding said DNA binding domain of said first transcription factor, which binding region is operatively linked to a minimal promoter that is operatively linked to an encoding region that encodes a polypeptide having tumor cell activity, which encoding region is operatively linked to a transcription-terminating region; and (b) exposing said cell to an effective expression-inducing dose of ionizing radiation;

whereby the polypeptide is expressed and inhibits the growth of said tumor.

3. The process according to claim 1, wherein the radiation responsive enhancer promoter comprises at least one distal CArG domain of an Egr-1 promoter, a tumor necrosis factor-α promoter or a c-Jun promoter.

4. The process according to claim 1, wherein the polypeptide is a tumor suppressing factor or an angiogenesis inhibitor.

5. The process according to claim 1, wherein said polypeptide is tumor necrosis factor-α, interleukin-4, JE, ricin, PF4 Pseudomonas toxin, p53, the retinoblastoma gene product or the Wilms' tumor gene product.

6. A process of treating a patient with a tumor comprising the steps of:

(a) delivering to said tumor in said patient a therapeutically effective amount of a DNA molecule comprising a radiation responsive enhancer-promoter operatively linked to an encoding region that encodes a polypeptide having the ability to affect the progression of said tumor; and (b) exposing said tumor to an effective expression-inducing dose of ionizing radiation;

whereby said tumor is treated.

7. The process according to claim 6 wherein the radiation responsive enhancer promoter comprises at least one distal CArG domain of an Egr-1 promoter, a tumor necrosis factor-α promoter or a c-Jun promoter.

8. The process according to claim 7 wherein the polypeptide is TNF-α.

9. The process according to claim 8, wherein the tumor is a sarcoma.

10. The process according to claim 9, wherein the tumor is in an animal.

11. The process according to claim 10, wherein the animal is a human.

12. A process of inhibiting growth of a sarcoma comprising the steps of:

(a) delivering to tie sarcoma a therapeutically effective amount of a DNA molecule comprising a least one distal CArG domain of an Egr-1 radiation responsive enhancer-promoter operatively linked to an encoding region that encodes TNF-α; and (b) exposing said sarcoma to an effective expression-inducing dose of ionizing radiation;

whereby TNF-α is expressed and the growth of said sarcoma is inhibited.

13. A method for expressing a mammalian structural gene in a cell comprising the steps of:

(a) incorporating into said cell a genetic construct comprising a plasmid comprising said structural gene operatively linked to the c-jun enhancer-promoter region, the TNF-α enhancer-promoter region or at least one distal portion of the Egr enhancer-promoter region; said enhancer-promoter inducible by ionizing radiation; and (b) exposing the genetic construct to ionizing radiation at a dose sufficient to induce expression of said structural gene.

14. The method according to claim 13, wherein the cell is a tumor cell.

15. The method according to claim 14, wherein the tumor cell is a human tumor cell.

\* \* \* \* \*

UNITED STATES PATENT AND TRADEMARK OFFICE
CERTIFICATE OF CORRECTION

PATENT NO.     :   5,770,581

DATED          :   June 23, 1998

INVENTOR(S)    :   Ralph R. Weichselbaum; Dennis E. Hallahan; Vikas P. Sukhatme; and Donald W. Kufe It is certified that errors appear in the above-identified patent and that said Letters Patent is hereby corrected as shown below:

In claim 2, line 31, before "activity" please insert --cytotoxic--.

In claim 12, line 3, please delete "tie" and insert therefore --the--.

Signed and Sealed this

Twenty-second Day of June, 1999

Attest:

Q. TODD DICKINSON

*Attesting Officer*     *Acting Commissioner of Patents and Trademarks*

UNITED STATES PATENT AND TRADEMARK OFFICE
CERTIFICATE OF CORRECTION

| | | |
|---|---|---|
| PATENT NO. | : | 5,770,581 |
| DATED | : | June 23, 1998 |
| INVENTOR(S) | : | Ralph R. Weichselbaum; Dennis E. Hallahan; Vikas P. Sukhatme; and Donald W. Kufe |

It is certified that errors appear in the above-identified patent and that said Letters Patent is hereby corrected as shown below:

In column 1, line 5, insert:

-- This invention was made with government support under grant numbers CA41068, CA42596, and CA58508 awarded by the National Institutes of Health. The government has certain rights in the invention. --

Signed and Sealed this

Twenty-fourth Day of August, 1999

Attest:

Q. TODD DICKINSON

*Attesting Officer*  *Acting Commissioner of Patents and Trademarks*